(12) United States Patent
Dolan et al.

(10) Patent No.: US 10,945,723 B2
(45) Date of Patent: Mar. 16, 2021

(54) SYSTEMS AND METHODS FOR SUTURING TISSUE

(71) Applicant: SafePath Medical, Inc., Amesbury, MA (US)

(72) Inventors: David P. Dolan, Londonderry, NH (US); Joseph P. Lane, Amesbury, MA (US)

(73) Assignee: SAFEPATH MEDICAL, INC., Amesbury, MA (US)

( * ) Notice: Subject to any disclaimer, the term of this patent is extended or adjusted under 35 U.S.C. 154(b) by 173 days.

(21) Appl. No.: 15/816,823

(22) Filed: Nov. 17, 2017

(65) Prior Publication Data

US 2018/0153540 A1 Jun. 7, 2018

Related U.S. Application Data

(60) Provisional application No. 62/423,493, filed on Nov. 17, 2016.

(51) Int. Cl.
| | |
|---|---|
| *A61B 17/04* | (2006.01) |
| *A61B 17/06* | (2006.01) |
| *A61B 17/062* | (2006.01) |
| *A61B 17/00* | (2006.01) |
| *A61B 17/29* | (2006.01) |

(52) U.S. Cl.
CPC ...... *A61B 17/0491* (2013.01); *A61B 17/0467* (2013.01); *A61B 17/0469* (2013.01); *A61B 17/062* (2013.01); *A61B 17/06109* (2013.01); *A61B 2017/00367* (2013.01); *A61B 2017/00535* (2013.01); *A61B 2017/00862* (2013.01); *A61B 2017/047* (2013.01); *A61B 2017/0608* (2013.01); *A61B 2017/2923* (2013.01)

(58) Field of Classification Search
CPC combination set(s) only.
See application file for complete search history.

(56) References Cited

U.S. PATENT DOCUMENTS

| | | | |
|---|---|---|---|
| 1,676,582 | A | 7/1928 | Stuart |
| 2,336,690 | A | 12/1943 | Karle |
| 4,109,428 | A | 8/1978 | Aarons |
| 4,373,530 | A | 2/1983 | Kilejian |

(Continued)

FOREIGN PATENT DOCUMENTS

| | | |
|---|---|---|
| GB | 630693 | 10/1949 |
| JP | 2009514562 | 4/2009 |

(Continued)

*Primary Examiner* — Tuan V Nguyen
(74) *Attorney, Agent, or Firm* — Leason Ellis LLP

(57) ABSTRACT

A device for suturing tissue includes a handle including a housing and a suturing needle for advancing a suture through the tissue. The device also includes a first needle gripper that is configured to both grasp and release the suturing needle. A second needle gripper is also configured to both grasp and release the suturing needle. An actuator is coupled to the housing and is operatively coupled to: (a) a first linkage that pivots the second gripping gripper between a fully extended position and a retracted position relative to the housing; and (b) a second linkage that is operatively coupled to the first and second needle grippers and configured to alter a state of each of the first and second needle grippers. The second linkage can include a one-way clutch.

41 Claims, 15 Drawing Sheets

(56) References Cited

U.S. PATENT DOCUMENTS

| | | |
|---|---|---|
| 4,406,237 A | 9/1983 | Eguchi et al. |
| 4,414,908 A | 11/1983 | Egochi et al. |
| 4,608,800 A | 9/1986 | Fredette |
| 4,621,640 A | 11/1986 | Mulhollan et al. |
| 4,935,027 A | 6/1990 | Yoon |
| 4,957,498 A | 9/1990 | Caspari et al. |
| 4,969,302 A | 11/1990 | Coggan et al. |
| 5,234,443 A | 8/1993 | Phan et al. |
| 5,426,901 A | 6/1995 | Indracek |
| 5,437,681 A | 8/1995 | Meade et al. |
| 5,454,823 A | 10/1995 | Richardson et al. |
| 5,499,990 A | 3/1996 | Schülken et al. |
| 5,571,090 A | 11/1996 | Sherts |
| 5,571,119 A | 11/1996 | Atala |
| 5,609,597 A | 3/1997 | Lehrer |
| 5,643,292 A | 7/1997 | Hart |
| 5,665,109 A | 9/1997 | Yoon |
| 5,694,726 A | 12/1997 | Wu |
| 5,709,693 A | 1/1998 | Taylor |
| 5,728,113 A | 3/1998 | Sherts |
| 5,729,933 A | 3/1998 | Strength |
| 5,730,747 A | 3/1998 | Ek et al. |
| 5,746,751 A | 5/1998 | Sherts |
| 5,759,188 A | 6/1998 | Yoon |
| 5,766,186 A | 6/1998 | Faraz et al. |
| 5,824,009 A | 10/1998 | Fokuda et al. |
| 5,843,100 A | 12/1998 | Meade |
| 5,860,992 A * | 1/1999 | Daniel ............... A61B 17/0469 606/139 |
| 5,871,488 A | 2/1999 | Tovey et al. |
| 5,891,160 A * | 4/1999 | Williamson, IV ........................ A61B 17/0469 112/169 |
| 5,897,563 A | 4/1999 | Yoon et al. |
| 5,904,692 A | 5/1999 | Steckel et al. |
| 5,908,428 A | 6/1999 | Scirica et al. |
| 5,919,202 A | 7/1999 | Yoon |
| 5,935,149 A | 8/1999 | Ek |
| 5,951,575 A | 9/1999 | Boldue et al. |
| 5,954,733 A | 9/1999 | Yoon |
| 5,957,937 A | 9/1999 | Yoon |
| 5,984,932 A | 11/1999 | Yoon |
| 5,993,466 A | 11/1999 | Yoon |
| 5,993,467 A | 11/1999 | Yoon |
| 6,026,616 A | 2/2000 | Gibson |
| 6,048,351 A | 4/2000 | Gordon et al. |
| 6,071,289 A | 6/2000 | Stefanchik et al. |
| 6,099,550 A | 8/2000 | Yoon |
| 6,099,553 A | 8/2000 | Hart et al. |
| 6,159,224 A | 12/2000 | Yoon |
| 6,224,614 B1 | 5/2001 | Yoon |
| 6,277,132 B1 | 8/2001 | Klaus Brhel |
| 6,533,795 B1 | 3/2003 | Tran et al. |
| 6,539,675 B1 | 4/2003 | Gile |
| 6,643,990 B2 | 11/2003 | Jensen |
| 6,911,034 B2 | 6/2005 | Nobles et al. |
| 6,923,819 B2 | 8/2005 | Meade et al. |
| 6,984,237 B2 | 1/2006 | Hatch et al. |
| 6,997,932 B2 | 2/2006 | Dreyfuss et al. |
| 7,011,668 B2 | 3/2006 | Sancoff et al. |
| 7,033,370 B2 | 4/2006 | Gordon et al. |
| 7,060,077 B2 | 6/2006 | Gordon et al. |
| 7,090,686 B2 | 8/2006 | Nobles et al. |
| 7,108,700 B2 | 9/2006 | Chan et al. |
| 7,188,454 B2 | 3/2007 | Mowery et al. |
| 7,316,694 B2 | 1/2008 | Reinitz |
| 7,318,282 B2 | 1/2008 | Pulte |
| 7,326,221 B2 | 2/2008 | Sakamoto et al. |
| 7,331,970 B2 | 2/2008 | Almodovar et al. |
| 7,338,504 B2 | 3/2008 | Gibbens et al. |
| 7,442,198 B2 | 10/2008 | Gellman et al. |
| 7,544,199 B2 | 6/2009 | Bain et al. |
| 7,572,265 B2 | 8/2009 | Stone et al. |
| 7,582,096 B2 | 9/2009 | Gellman et al. |
| 7,588,583 B2 | 9/2009 | Hamilton et al. |
| 7,615,059 B2 | 11/2009 | Watschke et al. |
| 7,628,796 B2 | 12/2009 | Shelton et al. |
| 7,704,262 B2 | 4/2010 | Bellafiore et al. |
| 7,748,179 B2 | 7/2010 | Schiedegger et al. |
| 7,793,475 B2 | 9/2010 | Riggs |
| 7,997,043 B1 | 8/2011 | MacMillan et al. |
| 7,998,149 B2 | 8/2011 | Hamilton et al. |
| 8,006,441 B2 | 8/2011 | Pulte |
| 8,172,860 B2 | 5/2012 | Zung et al. |
| 8,252,007 B2 | 8/2012 | Hamilton et al. |
| 8,257,371 B2 | 9/2012 | Hamilton et al. |
| 8,282,657 B2 | 10/2012 | McClurg et al. |
| 8,317,805 B2 | 11/2012 | Hamilton et al. |
| 8,419,754 B2 | 4/2013 | Laby et al. |
| 8,603,113 B2 | 12/2013 | Hamilton et al. |
| 8,617,187 B2 | 12/2013 | Hamilton et al. |
| 8,685,045 B2 | 4/2014 | Hamilton et al. |
| 8,758,391 B2 | 6/2014 | Swayze |
| 2002/0087178 A1 | 7/2002 | Nobles et al. |
| 2002/0088189 A1 | 7/2002 | Honda |
| 2002/0124485 A1 | 9/2002 | Pulte |
| 2003/0023250 A1 | 1/2003 | Watschke |
| 2003/0181926 A1 | 9/2003 | Dana |
| 2004/0092967 A1 | 5/2004 | Sancoff et al. |
| 2004/0243147 A1 | 12/2004 | Lipow |
| 2005/0043747 A1 | 2/2005 | Field et al. |
| 2005/0085857 A1 | 4/2005 | Peterson et al. |
| 2005/0119670 A1 | 6/2005 | Kerr |
| 2005/0125013 A1* | 6/2005 | Kessler ................. A61B 17/30 606/148 |
| 2005/0234479 A1 | 10/2005 | Hatch et al. |
| 2005/0267529 A1 | 12/2005 | Crockett et al. |
| 2006/0069396 A1 | 3/2006 | Meade et al. |
| 2006/0075712 A1 | 4/2006 | Gilbert et al. |
| 2006/0196144 A1 | 9/2006 | Spek |
| 2006/0282088 A1 | 12/2006 | Ryan |
| 2007/0021755 A1 | 1/2007 | Almodovar |
| 2007/0060930 A1 | 3/2007 | Hamilton et al. |
| 2007/0060931 A1 | 3/2007 | Hamilton et al. |
| 2007/0062140 A1 | 3/2007 | Sillik |
| 2007/0088372 A1 | 4/2007 | Gellman et al. |
| 2007/0225735 A1 | 9/2007 | Stone et al. |
| 2007/0270885 A1 | 11/2007 | Weinert et al. |
| 2008/0243147 A1 | 10/2008 | Hamilton et al. |
| 2008/0249545 A1 | 10/2008 | Shikhman |
| 2009/0012538 A1 | 1/2009 | Saliman et al. |
| 2009/0024145 A1 | 1/2009 | Meade et al. |
| 2009/0157105 A1 | 6/2009 | Zung et al. |
| 2009/0292300 A1 | 11/2009 | Hamilton et al. |
| 2010/0010512 A1 | 1/2010 | Taylor et al. |
| 2010/0016868 A1 | 1/2010 | Kim |
| 2010/0030238 A1 | 2/2010 | Viola et al. |
| 2010/0063519 A1 | 3/2010 | Park |
| 2010/0152751 A1 | 6/2010 | Meade et al. |
| 2010/0268257 A1 | 10/2010 | Hamilton et al. |
| 2010/0280530 A1 | 11/2010 | Hashiba |
| 2011/0251627 A1 | 10/2011 | Hamilton et al. |
| 2011/0313433 A1 | 12/2011 | Woodard, Jr. et al. |
| 2012/0165837 A1 | 6/2012 | Belman et al. |
| 2012/0316580 A1 | 12/2012 | Belman et al. |
| 2013/0041388 A1 | 2/2013 | Lane et al. |
| 2013/0165954 A1 | 6/2013 | Dreyfuss et al. |
| 2013/0231687 A1 | 9/2013 | Laby et al. |
| 2013/0245646 A1 | 9/2013 | Lane et al. |
| 2013/0267969 A1 | 10/2013 | Martin et al. |
| 2013/0304096 A1 | 11/2013 | Nguyen et al. |
| 2014/0222036 A1 | 8/2014 | Hamilton et al. |
| 2014/0276988 A1 | 9/2014 | Tagge et al. |
| 2014/0276989 A1 | 9/2014 | Lane et al. |
| 2014/0288581 A1 | 9/2014 | Hamilton et al. |
| 2015/0335326 A1 | 11/2015 | Dolan et al. |
| 2016/0015381 A1 | 1/2016 | Lane et al. |

FOREIGN PATENT DOCUMENTS

| | | |
|---|---|---|
| WO | WO 2010/011900 | 1/2010 |
| WO | WO 2013/025622 | 2/2013 |

(56) References Cited

FOREIGN PATENT DOCUMENTS

| | | |
|---|---|---|
| WO | WO 2013/126748 | 8/2013 |
| WO | WO 2015/179247 | 11/2015 |

* cited by examiner

SYSTEMS AND METHODS FOR SUTURING TISSUE

CROSS-REFERENCE TO RELATED PATENT APPLICATIONS

This application is based on and claims priority to U.S. Provisional Patent Application 62/423,493, filed Nov. 17, 2016, the entire contents of which is incorporated by reference herein as if expressly set forth in its respective entirety herein.

BACKGROUND

Needles and suture are used throughout the healthcare industry for indications such as wound and incision closure, securing catheters, and affixing implantable meshes, annuloplasty rings, and other medical apparatus. These sutures are used on the surface of the patient's skin as well as through laparoscopic, endoscopic, and surgical procedures. Because needles represent injury and illness risks to the user, there is a need to make needle usage safer without sacrificing ease of use, performance, and cost. A medical device that can be used to safely suture the tissue of a patient will be valuable to physicians, surgeons, nurses, physician assistants, military personnel, and other clinical and non-clinical users of suture.

SUMMARY

In one embodiment, a device for suturing tissue according to the present invention includes a handle including a housing having a distal end and an opposite proximal end and a suturing needle for advancing a suture through the tissue. The suturing needle has a first pointed end and an opposite second end. The device also includes a first needle gripper that is coupled to the housing and configured to both grasp and release the suturing needle. A second needle gripper is also coupled to the housing. The second needle gripper is configured to both grasp and release the suturing needle.

An actuator is coupled to the housing and is operatively coupled to: (a) a first linkage that pivots the second gripping gripper between a fully extended position and a retracted position relative to the housing; and (b) a second linkage that is operatively coupled to the first and second needle grippers and configured to alter a state of each of the first and second needle grippers to permit each respective needle gripper to either: (a) receive and grasp the suturing needle or (b) release the suturing needle. In accordance with one embodiment, the second linkage includes a one-way clutch that is operatively coupled to the actuator and is configured to synchronously alter the states of the first and second needle grippers to permit each respective needle gripper to either: (a) receive and grasp the suturing needle or (b) release the suturing needle.

The first linkage can include a plurality of gears that operatively couple the actuator to the second needle gripper such that motion of the actuator is translated into the second needle gripper rotating about a first pivot point between the fully extended position and a retracted position. In addition, the second linkage can include an energy storage mechanism that is configured to store energy during an inward stroke of the actuator and release the stored energy during one stage of an outstroke of the actuator, whereby the release of the stored energy causes the states of the first and second needle grippers to be altered.

In one embodiment, each of the first and second needle grippers comprises a first clamp and a second movable clamp that is pivotally attached to the first clamp at a pivot to permit the second movable clamp to pivot between open and closed positions, each of the first clamp and the second movable clamp defining a needle receiving groove in which the suturing needle is captured, the needle receiving grooves of the first clamp and the second movable clamp defining a needle receiving channel, wherein the first damp and the second movable clamp are adjustable relative to one another to permit a size of the needle receiving channel to be varied and set.

In one embodiment, a device for suturing tissue includes a handle formed of a housing having a distal end and an opposite proximal end, A suturing needle for advancing a suture through the tissue is provided and the suturing needle has a first pointed end and an opposite second end. The device also includes a first needle gripper coupled to the housing, with the first needle gripper being configured to both grasp and release the suturing needle. A second needle gripper is coupled to the housing, with the second needle gripper being configured to both grasp and release the suturing needle. The device also includes an actuator that is coupled to the housing. The actuator is configured such that operation of the actuator causes: (a) the second needle gripper to pivot between a fully extended position and a retracted position relative to the housing; and (b) a state of each of the first and second needle grippers to be altered to permit each respective needle gripper to either: (i) receive and grasp the suturing needle or (ii) release the suturing needle. The second linkage can include a one-way clutch that is operatively coupled to the actuator and is configured to synchronously alter the states of the first and second needle grippers to permit each respective needle gripper to either: (i) receive and grasp the suturing needle or (ii) release the suturing needle.

At least one of the first and second needle grippers includes a compliant structure formed along a needle receiving channel for influencing travel of the needle within the needle receiving channel. For example, the compliant structure can be a mass that is disposed within the needle receiving channel and axially aligned therewith such that one end (e.g., the pointed end) of the needle makes contact with the compliant structure during normal movement of the needle within the needle receiving channel, such as when the needle is transferred from one needle gripper from another and enters and travels within the needle receiving channel.

The device preferably includes additional features, such as a safety mechanism that shields the needle and a suture cutter.

BRIEF DESCRIPTION OF THE DRAWING FIGURES

DETAILED DESCRIPTION OF CERTAIN EMBODIMENTS

Figure 1A:
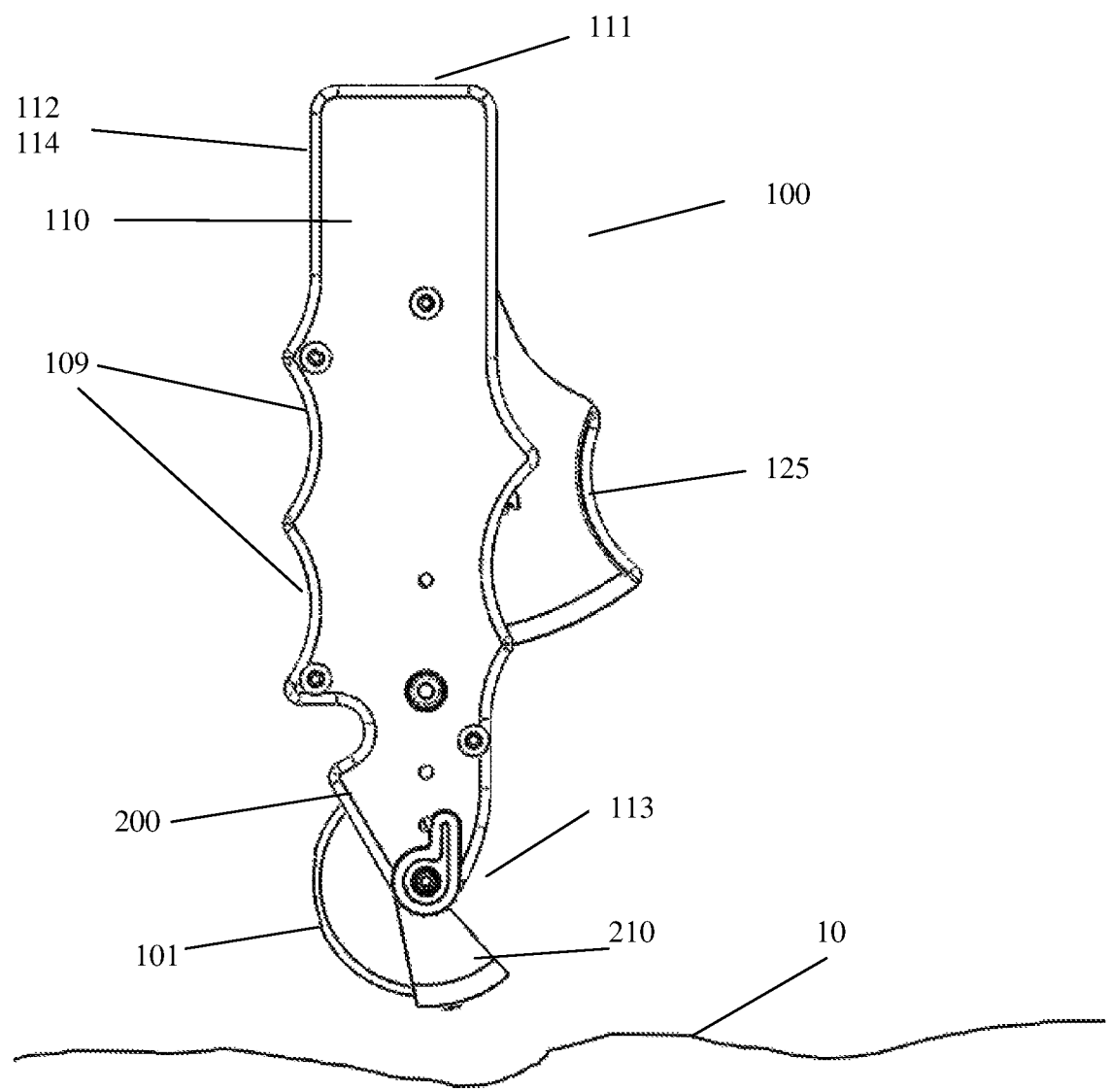
FIG. 1A is a side elevation view of a suturing device in a rest (packaged) position.

Disclosed herein are device concepts and methods for safely suturing tissue, skin, muscle, ligament, tendon and similar structures throughout the entire body. Healthcare workers need a safe method and device for closing wounds and incisions, approximating tissue, securing meshes and annuloplasty rings, securing catheters to a patient, and related functions. The current procedure typically consists of a user grasping an unprotected needle and suture with hemostats, a needle driver, forceps, or suturing device and then piercing the patient's tissue by utilizing hand, wrist, and device movements. In this scenario, the needle point is exposed to the user before, during, and after the procedure and provides risk for accidental needle stick injuries (NSI) to the user and procedural staff. These NSIs can transmit bloodborne pathogens such as hepatitis and HIV to the user and others from the patient and potentially cause illness or death. Users that are injured in this manner are required to report the injury, undergo diagnostic tests and begin receiving prophylactic treatment. They may also be required to take a leave of absence from work or continue indefinitely with a prescribed drug regimen.

A device according to one exemplary embodiment is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to a position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique that is familiar to a user based on experience with other surgical techniques.

In a preferred embodiment, the device has the following definitive advantages over current art: Safety: The user cannot contact the point of the needle and is able to avoid accidental NSIs and the human and financial costs associated with those accidents. Performance: The device allows the user to reproduce the needle delivery motion that is currently used by healthcare workers. This improves the accuracy and integrity of the securement and reduces the trauma to the patient. Size: The device is sized and oriented for easy access to crowded and narrow regions of the patient's body such as the neck; Ease of Use: The device can be generally operated with one hand, by right-handed and left handed users, and multiple sutures are able to be secured to the patient through a minimal series of steps. Cost: The device is designed as a single use device that is economical and easy to manufacture. Versatility: The device is suitable for use within a hospital environment and any first aid setting. It can be utilized to secure nearly every type of catheter and to close wounds. In addition, it may be packaged within catheter and medical accessory sets or as a stand-alone device.

In one exemplary embodiment, the needle within this device can be returned to its starting point after it crosses the patient's tissue so that the device can be used to repeat the needle delivery process multiple times. At the conclusion of the process, the needle is safely retained by a mechanism within the device, which can then be safely disposed. In this embodiment, safety features are incorporated into the device such that the user cannot come into contact with the needle before, during, and after the procedure. In addition, an integral cutter is incorporated into the device in order that the suture can be cut by the user without the need for scissors or a scalpel. At the conclusion of each suture delivery, the safety features are automatically engaged and needle is safely shielded from the user. Additional elements within this embodiment include an integral cutter in order that the suture can be cut or trimmed by the user without the need for a separate scissors or scalpel.

Although it is contemplated as a single-use device, it is understood that slight alterations can be made to the design and materials that would allow said device to be resterilized, reloaded with an additional needle and suture, and reused. It may be further contemplated that the distally mounted needle has the ability to rotate relative to the handle and replicate the manual needle-driving motion of crossing tissue that is currently used in and outside the clinic. This is particularly useful in laparoscopic, endoscopic, and surgical procedures when the user's natural range of motion is compromised.

Looking again at the primary embodiment, the handle, which is comprised of one or more components such as a housing, actuator, and buttons, may be molded, cast or extruded from a variety of materials including but not limited to polymers or metals. Examples of polymers suitable for fabricating the handle are thermoplastic and thermosetting materials such as polystyrene, acrylic, polycarbonate, polyamide, polyester, polyetherimide, polysulfone, polylactic acid, polyvinylchloride, polyolefins, polyurethane, fluoropolymers, and copolymers and alloys thereof. These materials may be filled with glass or other useful reinforcing agents in order to enhance their mechanical properties. Suitable metals come from but are not limited to a group including titanium alloys and stainless steel. The selected materials must meet physical and mechanical performance requirements and be able to withstand sterilization methods employed within the medical device industry such as ethylene oxide or gamma irradiation. The handle design may be constructed to be linear and longitudinal, non-planar, angled, arcuate or a combination of these conformations.

The needle assembly generally consists of a suturing needle and a suture attached thereto. The suturing needle includes a distal pointed end suitable for piercing and crossing tissue and a blunt proximal end suitable for affixing a suture, and a body between the distal and proximal ends. The suturing needle can be fabricated in a variety of configurations from straight to curved and be monolithic, channel-bodied or of a multi-part construction. The outer diameters of the needles can be round or non-round, tapered, or possesses features that assist in advancing and gripping the needle, i.e., flats, ribs, corners. Longitudinal ribs or recessions or other features found on the outer diameter of the needle may provide additional rigidity and enhance the needle's ability to effectively cross tissue. Needles are commonly made from stainless steel and related alloys but can be made from other metals, polymers and ceramic materials that are sufficiently rigid, capable of possessing and sustaining a functionally sharp distal point, and able to attach to suture. Traditionally, sutures are affixed to the proximal end of metal needles by swaging, crimping, knotting and adhesives. Suture attachment can also be configured such that the suture is affixed to the other regions of the needle, yet not the proximal terminus. This design variant provides additional freedom for suture management and gripping the needle in the device handle. In this configuration, attachment of the suture can be made by swaging, crimping, knotting, adhesives, etc. Coatings on the needle serve to enhance the lubricity of the needle and reduce tissue penetration forces.

The suture is the thread-like material that is used to treat internal and external wounds and incisions and to secure catheters or other components to patients. It comes in a variety of diameters, textures, forms, i.e., single strand or braided, and materials depending upon the desired properties and intended application. Sutures can be absorbable, i.e., collagen, polyglactin, polydioxanone, polyglycolide-lactide copolymers, or non-absorbable, i.e., silk, nylon, polyester, polypropylene, stainless steel. They can be treated with antimicrobial, bioabsorbable, hydrophilic or other functional additives. In addition, they can have surface features, e.g., barbs, that permit the suture to be drawn smoothly through tissue in one direction but snag the tissue when pulled in the opposite direction. This is advantageous when the user wants to temporarily or permanently approximate tissue without the need to tie a traditional knot.

The interfaces between the handle and the suturing needle/suture are generally referred to as the mechanisms or assemblies. These mechanisms serve to grasp, release, and shuttle the needle by manipulations to the handle by the user or by otherwise manipulating the device to cause the needle transfer. As will be appreciated from the detailed description below, there are a number of mechanical mechanisms that can be used to produce the desired movement of the suturing needle and more specifically, produce a reciprocal needle transfer action in which the suturing needle is initially held in one position within the mechanism and is then caused to be moved to another position within the mechanism to effectuate the suture needle passing into and through the tissue and then being subsequently extracted from the tissue. Further, after extraction, the mechanism is preferably designed to pass the suturing needle back from the needle capture/extraction position to the initial position at which the entire process can be repeated. Thus, one mechanism can be thought of as being a mechanism for cycling the suturing needle between different positions that result in the desired suturing action.

In addition, as used herein, the term "linkage" refers broadly to one or more parts that serve to link one part to another part. For example and as described herein, the actuator of the device is operatively connected to a number of other parts, assemblies or mechanisms by means of one or more linkages as set forth in greater detail herein.

It will thus be appreciated that a variety of mechanisms that are able to grasp, release, and shuttle the needle can be used. The mechanisms include but are not limited to rack and pinion, gearing, cams, ramps, screw bodies, springs, multiple-point gripping structures, i.e., 3-point, collets, drive belts, and rigid and flexible push rods to name a few. In instances, the suturing needle can comprise physical features that correspond to engagement features found within these mechanisms in order, for example, to increase grip strength. Some examples of these features are indentations, serrations, projections, faces, flats, undercuts, rings, and ports.

Moreover, the present device preferably includes a safety shield mechanism, which protects the user from the needle point before, during, and after the suturing procedure. The safety shield mechanism can exist in numerous forms in that any number of different mechanical arrangements can be used to accomplish the intended function. The safety shield mechanism can comprise single or multiple components, be biased to a safety-mode position and/or be user actuated, and/or have reversible or irreversible lock-out features. The safety shield mechanism can be configured, for example, as a slideable or rotatable cover, or as deflectable wing-like shields that obstruct user access to the needle point. Similar to the handle described above, the safety shield mechanism cans be made from a wide range of thermoplastics and thermosetting polymers. Furthermore, the safety shield mechanism can be manufactured from metals, such as stainless steel, titanium, and titanium alloys including nickel-titanium, and configured as a wire-form, mesh, grid, strut, or other structural forms. A spring or other force-resilient components can be incorporated in order to bias the safety apparatus into a safe position or to actuate multiple components that comprise the safety apparatus.

Referring to the lockout feature above, it will prevent the user from accidentally exposing the needle and obtaining an NSI. The lockout generally takes the form of a user-actuated button, lever, slide, or other similar means and a connecting element that couples the actuation means and the safety apparatus. The button causes the connecting element to lock and unlock the apparatus in a variety of ways. Examples of these means include tongue and groove, intermeshing gears, friction and interference fits, inclined planes, cantilever, and screws. In each of these methods, the connecting element restricts the movement of the apparatus, and therefore, the exposure of the needle until the user actuates the button to release the apparatus.

Finally, a suture cutter is preferably located within the device handle so that the user can trim knotted sutures and suture strands to length. One exemplary cutter can be a dynamic shearing apparatus, i.e., scissors or slideable blade(s), that requires the user to press or slide a button or manipulate an actuator having a different form, such as a knob or lever, in order to actuate the blade to cut the suture. To this end, the suture(s) can be positioned in a notch, slot, or hole located on the handle, and the actuation of the sharpened blade would cut the suture(s). Upon cutting the suture, a spring or similar biasing component would return the blade to its original position such that the cutting process can be repeated. The blade may traverse the suture cutting region with a linear, arcuate, or combination of these motions. Alternatively, the cutter can be a simple apparatus such as a static cutting blade located in a narrowing, crevice-like feature on the handle. In this configuration, the suture could be drawn across the sharp edge of the blade in order to cut it. Typical materials that are useful as cutting blades are stainless steel, carbon steel, and gemstones, such as diamond. For safety purposes, the user does not have direct access to the cutting blade; only suture is able to reach the blade via the suture cutter notch or hole. Beyond the safety advantage, the integral cutter would reduce or eliminate the need for the user to provide a separate pair of scissors for cutting or trimming suture during the procedure.

It will be appreciated that the above-described structures constitute exemplary parts of one suturing device according to the present invention and each of these structures is described in greater detail below. The foregoing discussion is thus a brief summary of suitable parts that can be present within the present suturing device; however, they are not to be considered to be limiting of the scope of the present invention. The make-up and operation of various exemplary suturing devices in accordance with the present invention are now described.

Referring to FIGS. 1a-1f, a suturing device 100 in accordance with a first embodiment includes a housing 110 that contains a number of the working components and allows a user to easily hold and use the suturing device 100. For example and as shown in the illustrated embodiment, the housing 110 can be in the form of an elongated handle that is formed of a first proximal end 111 and a second distal end 113. The housing 110 includes first and second parts 112, 114 are complementary to one another and include a means for attaching the two parts 112, 114 together to form an assembled handle 110 that can be easily grasped and manipulated by the user. For example, the first and second parts 112, 114 can be attached to one another by a mechanical attachment, such as by using fasteners (e.g., screws, bolts, etc.), by establishing a snap-fit between the two parts, welding (e.g., sonic, spin, etc. . . . ) or by another technique. The handle 110 not only houses many of the working components but also provides a means for the user to grasp the device 100 but also manipulate it in such a way to cause a needle 101 to be advanced into and through the tissue 10 and then exit the tissue 10.

Each of the first and second parts 112, 114 is generally hollow (e.g., a hollow shell) and therefore, when the two handle parts 112, 114 are attached to one another, they define a hollow interior handle space that receives and holds many of the working components of the device 100 as will be appreciated below. It can be further appreciated that the handle parts 112, 114 can house the many working components of the device and in another embodiment they can also contain an inner frame or frame halves that hold many or all of the working parts of the device. This alternative design can provide benefits to the device performance and the manufacturing assembly process. Therefore, future reference to handle parts 112, 114 can imply that the handle body is comprised of two or more parts. The handle 110 can include ergonomic gripping regions/surfaces 109 suitable for both left and right-handed users to facilitate grasping of the device 100. As shown, these gripping regions 109 can be in the form of locally recessed and contoured portions of the handle 110 that locate and permit a user's thumb/fingers to grasp the exterior of the device 100. The gripping regions 109 can alternatively be defined by a modified exterior surface of the housing parts 112, 114 within local handle sections that allow the user to more easily grasp the handle. For example, the exterior surface of one or both of the handle parts 112, 114 can be a rough surface defined by surface features, such as a plurality of raised bumps or the like or can even be defined by a material that is different than the material of the handle and is applied thereto (e.g., a gripping surface member applied to the handle 110 by means of an adhesive or over-molding process or other suitable process). Additional examples of surface gripping features include but are not limited to loops, hooks and rings. Thumb loop 127 (FIG. 2B) is one such specific example.

As shown in the figures and described in detail herein, the suturing device 100 is configured to move a curved suturing needle 101 in a controlled manner such that the suturing needle 101 is advanced into and through target tissue 10 and is then extracted from the tissue 10 to complete one suturing action and allow the user to tie off the suture element 102 itself. As mentioned herein, any number of different types of suturing needles 101 can be used with the device. In general, the suturing needle 101 includes a sharp distal end 103 for penetrating the tissue 10 and an opposite proximal end 106, which is typically a blunt end.

The device 100 also includes an actuator assembly 125 that is used to operate the device and to effectuate the controlled movement (shuttle action) of the suturing needle 101 and cause the suturing needle 101 to be driven into and then extracted from the tissue 10. The actuator assembly 125 includes an actuator body 126 that is accessible to the user and is manipulated by the user to cause controlled movement of the suturing needle 101. In the illustrated embodiment, the actuator body 126 extends from the side of the handle 110 and is accessible by the user. The actuator body 126 is operatively coupled to other parts of the actuator assembly 125 to cause the desired controlled movement as described herein below and in particular, causes needle transfer to effectuate the suturing action.

It will be appreciated that the illustrated actuator assembly 125 is merely one exemplary type of actuator that can be used in the present device to cause controlled movement of the suturing needle 101 and there are a number of other actuator assemblies that can be used for causing the needle 101 to be transferred (shuttled) in the manner described herein. For example, while the actuator body 126 is pivotably rotated by the user (e.g., as by pressing the body 126 into the hollow interior of the handle 110), other actuators suitable for use in the present invention can be activated by other techniques, such as pressing a button or linear slide, rotating an actuator element, etc. In addition, the actuator body 126 is not limited to traveling within the hollow interior of the handle 110 but instead can travel a long an outer surface of the handle 110. Thus, the actuator could be mounted on any number of the available surfaces on the device 100. The actuator assembly 125 or the actuator body 126 could also be comprised of multiple sections, i.e., two conjoined halves. In addition, in other embodiments, the actuator can be driven linearly instead of in a sweeping, pivoting motion.

The needle transfer mechanism is comprised of two primary sub-mechanisms: a first gripping mechanism (first needle gripper or fixed clamp) 200 and a second gripping mechanism (second needle gripper or catch arm) 210. The first gripping mechanism 200 firmly holds the needle 101 and allows the user to penetrate tissue 10 and also to receive the needle 101 from the second gripping mechanism 210 in order to deliver additional sutures. The second gripping mechanism 210 serves to cover the sharp distal 103 end of the needle 101 while the device 100 is in its packaged and reset condition, and the second gripping mechanism 210 also serves to actively extract the needle 101 from tissue 10. The first gripping mechanism 200 is generally stationary within the handle 110, while the second gripping mechanism 210 is generally movable relative to the first gripping mechanism 200 and handle 110 to allow for transfer (shuttling) of the needle 101 between the first and second gripping mechanisms 200, 210.

In the illustrated embodiment, the actuator body 126 extends from one side of the handle body and is operatively connected to a needle transfer mechanism, which as mentioned herein, is designed to controllably move the needle 101 from one operating position to another operating position and more specifically, to transfer the suturing needle 101 from one needle gripping mechanism 200, 210 to the other mechanism 200, 210 to allow the suturing needle 101 to be extracted from the tissue 10 once it passes therethrough.

Continuing with FIGS. 1*a*-1*f*, the general operation of a suturing device 100 is depicted. Please note that not all features, i.e., suture cutters, depth controllers, safety apparatus, are shown in these figures. They are presented in separate figures and described in detail with reference to these other figures.

Figure 1B:
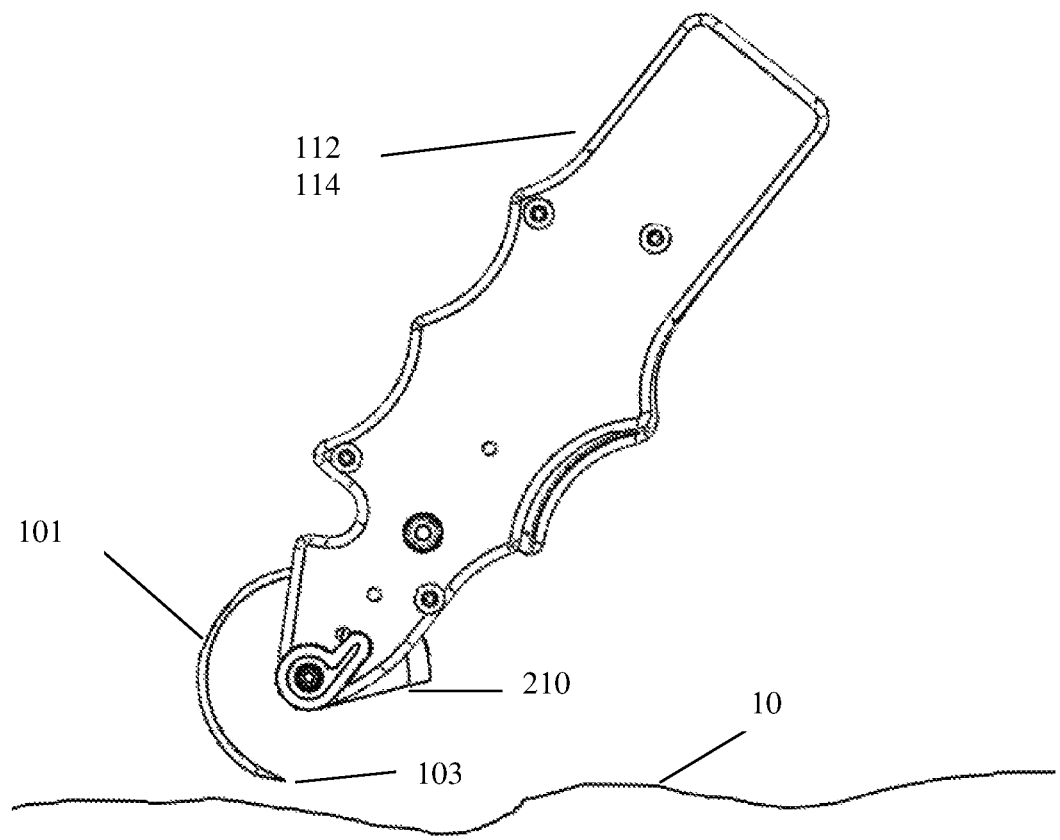
FIG. 1B is a side elevation view of the suturing device with a movable gripping mechanism in a retracted position after completion of an inward stroke of an actuator to expose a needle.
Figure 1C:
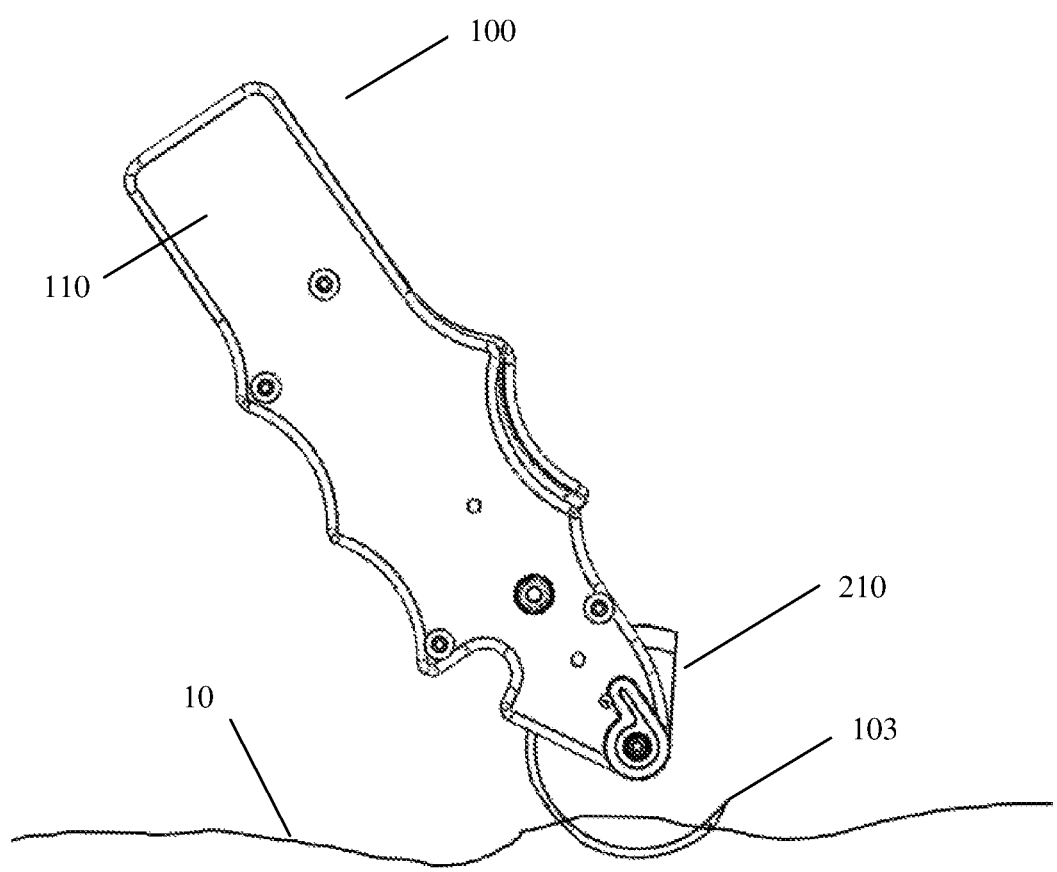
FIG. 1C is a side elevation view of the suturing device pivoted such that the needle penetrates and exits tissue.
Figure 1D:
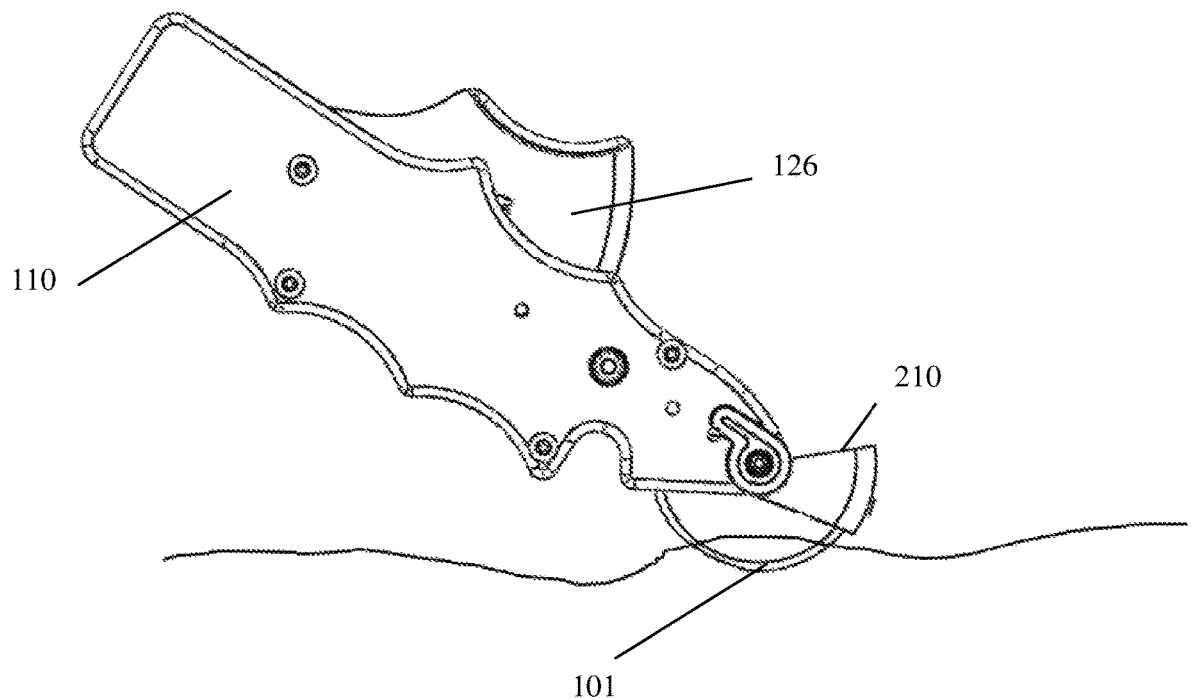
FIG. 1D is a side elevation view of the suturing device after the movable gripping mechanism returns to its extended state and grips the needle upon completion of an outstroke of the actuator.
Figure 1E:
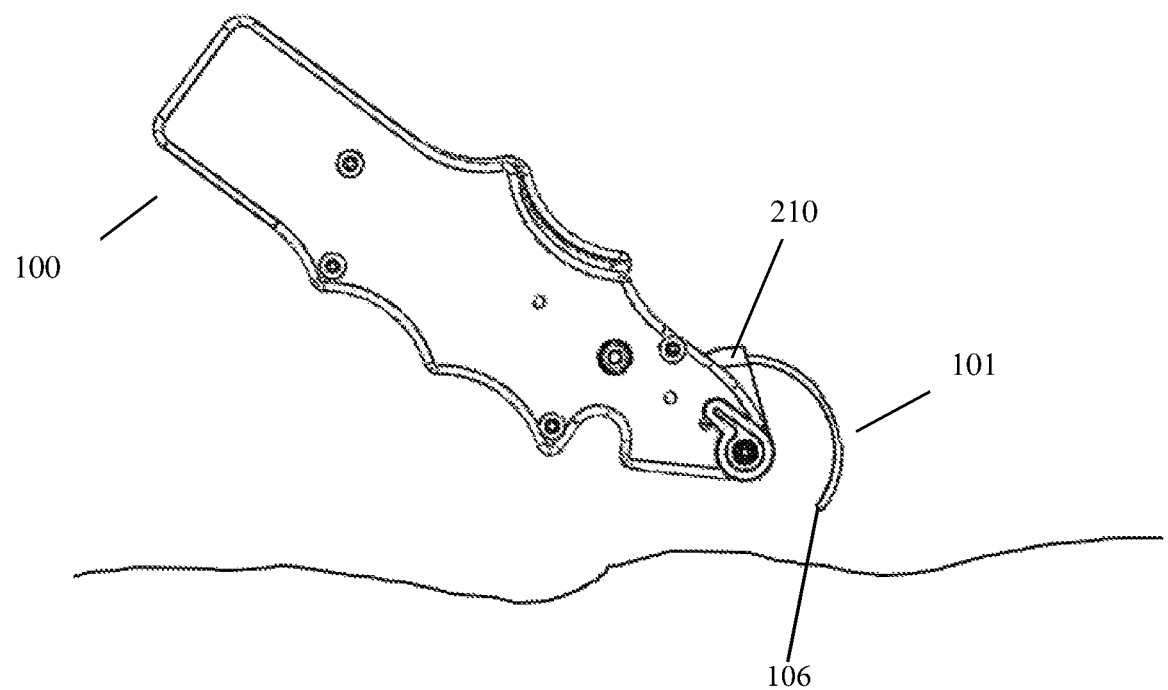
FIG. 1E is a side elevation view of the suturing device after a second inward stroke of the actuator is completed resulting in the needle being extracted from the tissue.
Figure 1F:
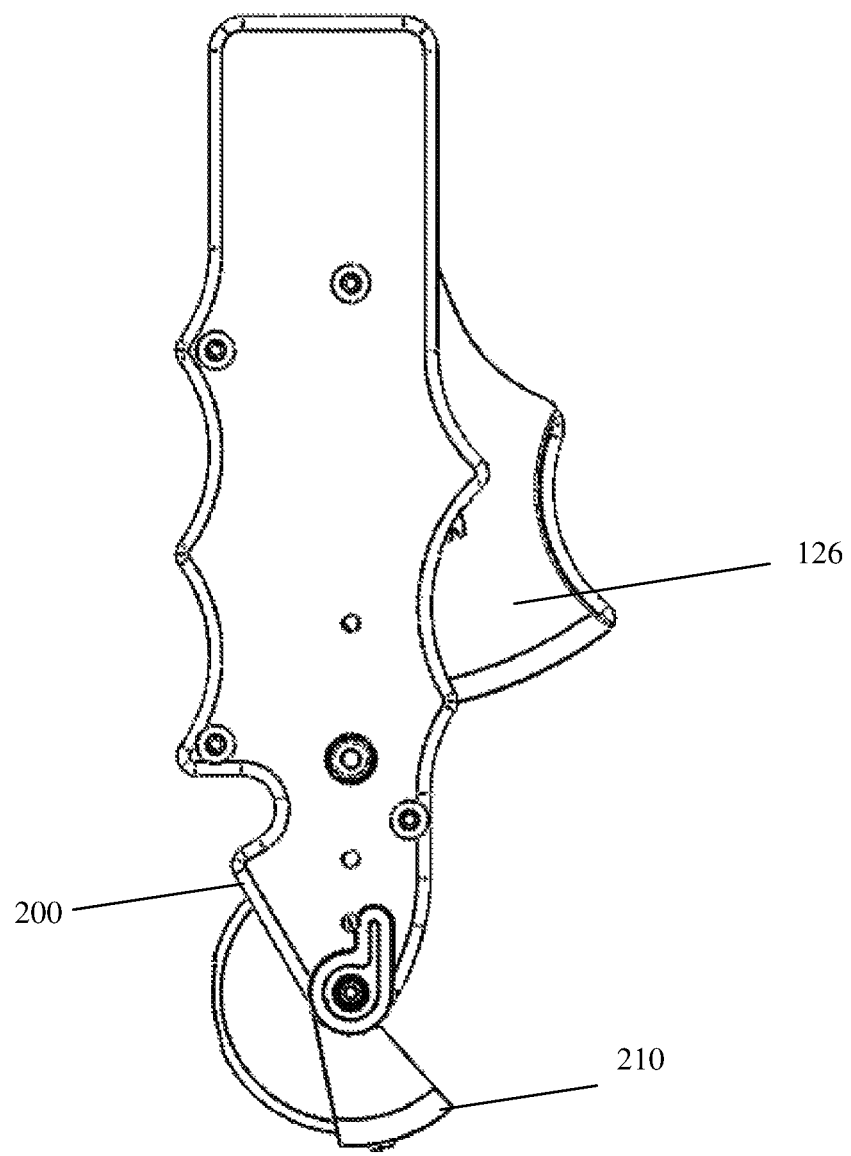
FIG. 1F is a side elevation view of the suturing device after an outstroke of the actuator is completed resulting in the needle being returned to the initial position.

FIG. 1A shows the device in its packaged condition (initial rest position) with the first gripping mechanism 200 having a firm grasp of the blunt end of the needle 101. The needle point 103 is covered by the second gripping mechanism 210 and is exposed when the user depresses the actuator 125 (inward stroke of the actuator 125 which results in a sweeping, non-linear motion of the actuator). The user can now penetrate the patient's tissue 10 with the needle 101 by orienting the handle 110 such that the needle point 103 is positioned to catch and pierce the tissue 10 as seen in FIG. 1B. Once the needle 101 is properly oriented, the user rotates his wrist such that the needle 101 penetrates and exits the tissue 10 as presented in FIG. 1C. When the needle 101 exits the tissue 10, a safety guard (not shown but illustrated in other figures) shields the needle point 103 and protects the user from injury. FIG. 1D depicts the second gripping mechanism 210 capturing the pointed end 103 of the needle 101 when the user releases the actuator assembly 125 (return stroke or out stroke of the actuator). With the needle 101 now gripped by the second gripping mechanism 210, the user can depress the actuator assembly 125 (a second inward stroke) in order to actively extract the needle 101 from the tissue 10 as seen in FIG. 1E. Finally, in FIG. 1F the user releases the actuator assembly 125 (a second return stroke or out stroke) and the needle 101 is rotated back to its origin, allowing the user to repeat the suture delivery process. The user may also activate the integral suture cutter (not shown) to cut the suture 102 to length or to trim the knotted suture.

In a preferred embodiment the device 100 is provided sterile in packaging, such as a blister pack, pouch, or similar. The device 100 comes out of the package in an at-rest condition where the needle 101 is gripped by the first gripping mechanism 200 near the distal end of the device 100, and the second gripping mechanism 210 is in its at-rest position enclosing the distal end of the needle 103, but not gripping the needle 101. The needle 101 features a length of suture 102 from its mid-section.

The device 100 is constructed such that the actuator assembly 125 is operatively connected to a mechanism (linkage) that translates the movement of the actuator assembly 125 into controlled movement of the first and second gripping mechanisms 200, 210 in the manner described with reference to FIGS. 1*a*-1*f*.

Figure 2A:
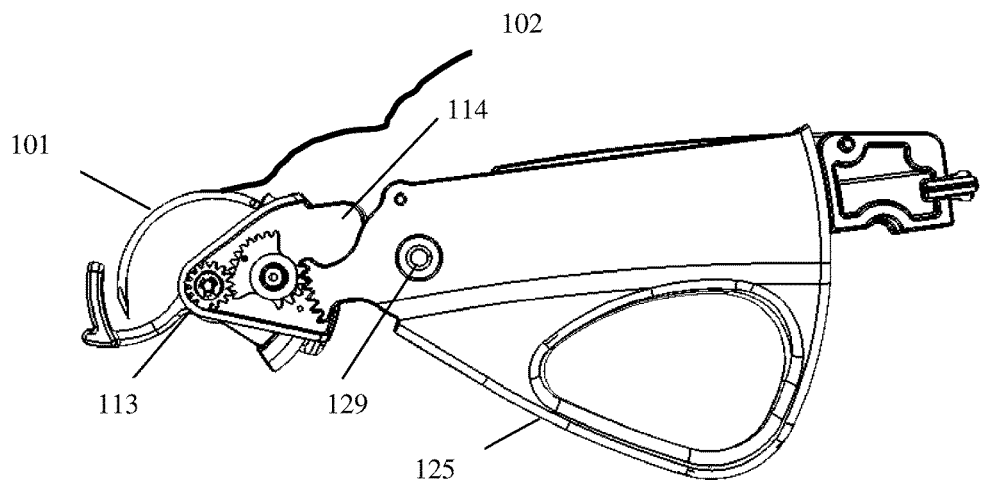
FIG. 2A is a side elevation view of a suturing device according to one embodiment showing a first linkage and actuator for causing rotation of a first needle gripper.
Figure 2B:
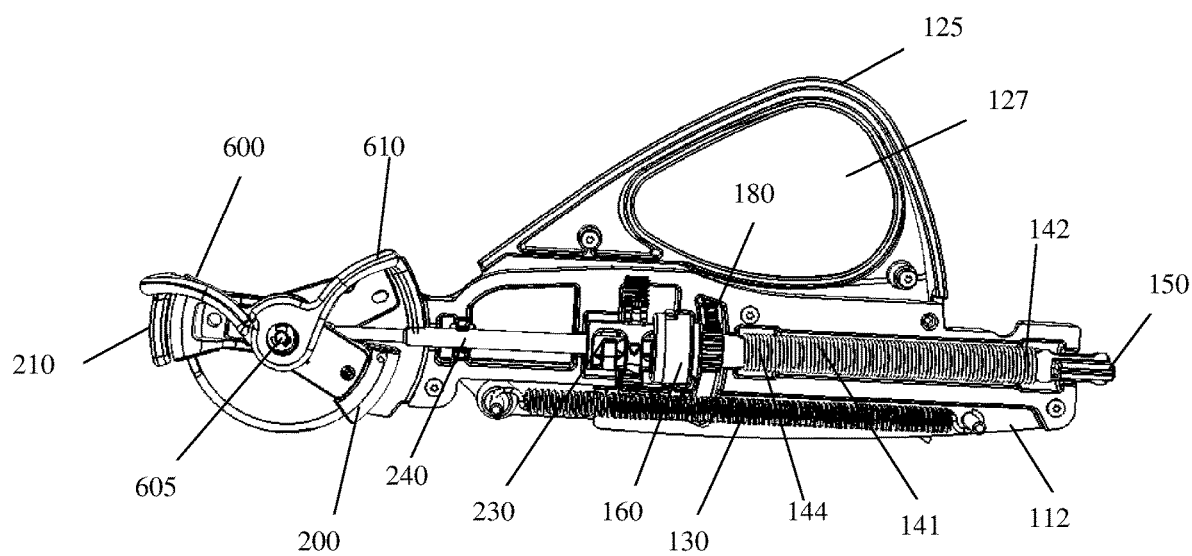
FIG. 2B is a side elevation view of the suturing device of FIG. 2A with part of the housing removed to show internal working components thereof.
Figure 2C:
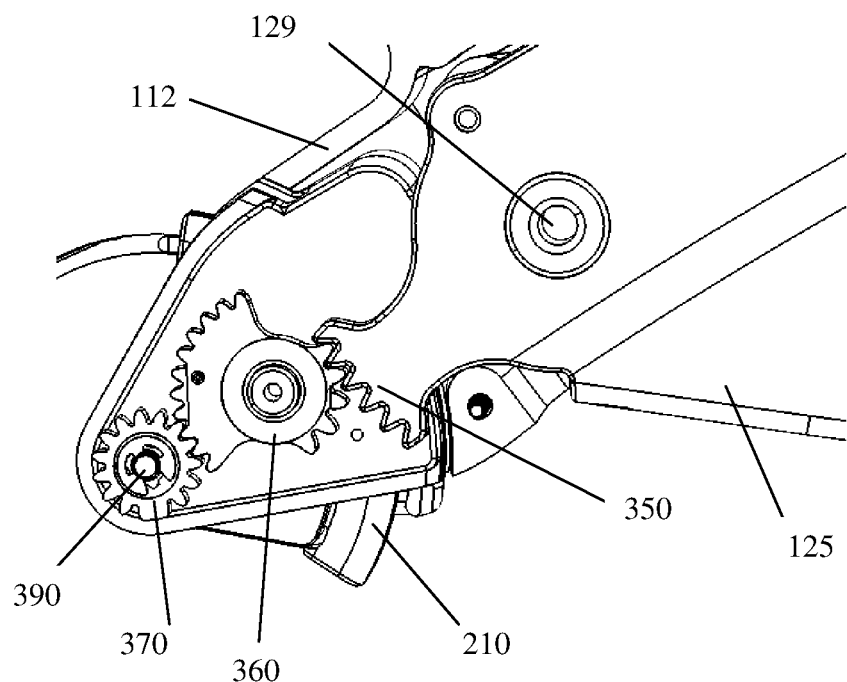
FIG. 2C is a close-up of the first linkage and a portion of the actuator.

FIGS. 2*a*-2*c* show a suturing device that is similar to suturing device 100 according to one embodiment. In this embodiment, the actuator assembly 125 protrudes from the side of the housing 110 and swings (pivots) in an arcing motion from a first at-rest position to a mechanically limited, end-of-travel second position partially or fully inside or outside of the housing when squeezed by the user (i.e., an inward stroke of the actuator). A return spring 130 biases the actuator 125 toward the at-rest position and offers resistance to the user when squeezing. The return spring 130 is disposed within the hollow interior of the handle body. For example, the return spring 130 can be in the form of an elongated spring that has one end coupled to a first structure, such as the handle and an opposite end that is coupled to the actuator assembly 125. The return spring 130 is configured such that when an inwardly directed force is applied to the actuator body 126 to cause the actuator body to pivot, the return spring 130 stores energy. After removal of the inward directed force (at the physical end of the inward stroke of the actuator body 126 or at a partial inward stroke), the energy stored in the return spring 130 is released and the actuator undergoes an outstroke movement and returns to the initial rest position.

The actuator assembly 125 is connected to the second gripping mechanism 210 by mechanical means (gears, linkages, pulleys, belts, cables or other means known to the art) such that when the actuator assembly 125 moves from its at-rest position to its fully depressed position, the second gripping means 210 moves proportionally from its at-rest position to its fully retracted position. In this embodiment, the gear train connecting the actuator assembly 125 and the second gripping mechanism 210 has approximately an 8:1 ratio; about 20 degree rotation of the actuator assembly 125 results in about 160 degree rotation of the second gripping mechanism 210. Of course, alternative gear count, size and ratios could be employed to accomplish the dynamic relationship between the actuator and second gripping means. In the at-rest position, the second gripping mechanism 210 can be thought of as being in a 6 o'clock position, and in the fully retracted position, the second gripping mechanism 210 can be thought of as being in an approximately 1 o'clock position.

Further, the actuator assembly 125 features a first gear portion 350, which moves in unison with the actuator body 126 (alternatively, the gear portion may also be a separate element that is fixedly connected to the actuator body 126). The first gear portion 350 thus pivots about pivot 129 and includes teeth that face the second end 113 of the housing 110. The teeth of the first gear portion 350 mesh with a first set of teeth that belong to a second gear 360 that is pivotally mounted to the housing 110 and spaced from the actuator body 126. The second gear 360 also includes a second set of teeth that face the second end (distal end) 113 of the housing 110. The second gear 360 can be in the form of a reducer gear that can accomplish the approximately 8:1 ratio mentioned above. The second set of teeth of the reducer gear 360 mesh with teeth of a third gear 370 which pivots about an axle 390. The third gear 370 is fixedly coupled to the movable second gripping mechanism 210 and therefore, rotation of the third gear 370 results in rotation of the second gripping mechanism 210 and in this manner, the second gripping mechanism 210 can move across the range of motion shown in FIGS. 1a-f.

It will be appreciated that one function of the actuator assembly 125 is to move the second gripping mechanism 210 in a pivoting manner. In both the inward stroke and the out stroke of the actuator 125, the motion of the actuator 125 is directly translated into pivoting of the second gripping mechanism 210 due to the action of gears 350, 360, 370 (which can be considered a linkage that operatively connects the actuator with the second gripping mechanism).

A second function of the actuator 125 will now be described and in particular, this second function deals with the alternating opening and closing of the first and second gripping mechanisms 200, 210 to facilitate the transfer of the needle 101 between the two mechanisms 200, 210 as a result of an energy transfer mechanism. In other words, the states (open or closed) of the first and second gripping mechanisms 200, 210 are altered by action of the actuator assembly 125.

The actuator assembly 125 is also connected (by gears or other means) to an energy storage device (member) 140. In one embodiment, this energy storage device 140 is a torsion spring 141.

It will be appreciated that the device 100 can utilize other mechanisms instead of the torsion spring 141 shown in the figures so long as these mechanisms provide the desired movements as described herein. For example, other embodiments can incorporate and be based on other kinds of springs, air compressing pistons, fly wheels, opposing magnets or any other energy storage means known to the art.

The torsion spring 141 is an elongated structure that has a first end 142 and an opposite second 144. Like the return spring 130, the torsion spring 141 is disposed within the hollow interior of the handle body and as shown, the return spring 130 and the torsion spring 141 can be disposed parallel to one another. The two springs 130, 141 can be located substantially side-by-side and they can partially overlap one another.

The torsion spring 141 can be coupled to a first mount 150 that is located at the first end 142 of the torsion spring 141 and a second mount (connector) 160 that is located at the second end of the torsion spring 141. The mount 150 is a fixed structure in that it does not rotate during operation of the device and serves as means for fixing the first end of the torsion spring 141 to the surrounding structure. Conversely, the second mount 160 moves with the torsion spring 141 and thus, both the torsion spring 141 and the second mount 160 are free to rotate in a first direction as the torsion spring stores energy and both are free to rotate in a second direction as the torsion spring 141 releases energy. As a result, when the second mount 160 is driven (rotated), as described below, the torsion spring 141 is likewise driven (rotated) in the same direction. Conversely, when the stored energy is released and the torsion spring 141 rotates and unwinds, the second mount 160 likewise rotates in the same direction. In one embodiment, the first mount is a spring winder 150 and the second mount is a pinion gear 160.

Both mounts 150, 160 can be in the form of a circumferential structure, or other appropriately useful configuration (shape), that can be disposed about the ends of the torsion spring 144, 142.

The internal energy transfer mechanism includes a pinion gear 160 which is fixedly connected to the torsion spring 141 by means of a feature, such as a grooved post 161 in this embodiment or other coupling mechanisms such as a collet, screw thread, press-fit, snap-fit, etc. . . . . The pinion gear 160 is driven by a rack 180 that is coupled to (but separate from) the actuator body 126 such that the actuator body 126 and rack 180 move together. The rack always remains coupled to the pinion gear 160. As shown in FIG. 2A-2B, the actuator body 126 can pivot (rotate) about a pivot point 129. The rack 180 can also rotate about the axis defined by the pivot point 129, with or without physical contact with the pivot point 129. Alternatively, the rack 180 can engage and affect the pinion gear 160 in a non-pivoting manner, e.g., linear translation. On the inward stroke, the actuator 125 contacts and pushes the rack 180. A partial stroke and release causes the rack 180 to rotate the pinion 160 but then reverse due to the torsion spring 141. During a full inward stroke, the rack 180 remains with the pinion gear 160 when the pawl 220 (described herein) locks the windup mechanism (described herein) in a cocked position. The return spring 130 alone creates the outstroke of the actuator assembly 125. In this embodiment, the return spring 130 is fixedly mounted to the housing 110 and the actuator assembly 125, although other mounting configurations can be appreciated. Since the rack 180 is not directly connected to the actuator body 126, the rack 180 stays in place in the cocked position during the out stroke of the actuator assembly 125 until the stored energy of the windup mechanism is released at which time, the rack 180 returns to its first (initial) position.

Alternatively, it has been contemplated to eliminate the return spring 130 and for the user to control the instroke and outstroke of the actuator 125 with his thumb and finger(s). An array of loops, similar to thumb loop 127, or other grasping means, can facilitate that design.

The rack 180 contains teeth that intimately mesh with the teeth of the pinion gear 160. As a result, when the rack 180 rotates about the axis of the pivot point 129, it directly translates into rotation of the pinion gear 160. This rotation of the pinion gear 160 is translated into rotation of the torsion spring 141 and depending upon the direction that the pinion gear 160 is rotated, the torsion spring 141 will either windup and store energy or wind-down and release (decrease) stored energy. In particular, the pinion gear 160 is wound-up one half turn by the rack 180 when the actuator 125 is depressed fully (a full inward stroke of the actuator), and is configured to hold the stored energy of this half turn when the actuator 125 reaches its fully depressed position.

It will be appreciated that the rack 180 alternatively can exist in different configurations (L-shaped, etc. . . . ), which may or may not share a pivot with the actuator 125.

Looking at FIGS. 3a-4d, the pinion gear 160 of the energy transfer mechanism is configured to have a generally hollow body that includes a first end 192 and an opposite second end 194, with the first end 192 facing the torsion spring 141. As described herein, the pinion gear 160 is disposed within the housing 110 in such a way that it has controlled rotation therein during the inward stroke and a subsequent out stroke. As used herein, the "windup mechanism" comprises the torsion spring 141, mount 150, and the pinion gear 160.

The interior of the pinion gear 160 includes a first notch 191 and a second notch (not shown) that is spaced from the first notch 191. For ease of illustration, the two notches will be discussed as being notches 191 since they are of the same construction but just spatially offset from one another. The first and second notches 191 can be formed about 180 degrees from one another. Alternatively, notches 191 can be windows, ratchets or other features that recess or stand proud of the interior of the pinion gear. The exterior of the pinion gear features two cam ribs 195, 197 that wrap circumferentially and independently around the second end 194 of the pinion gear 160. These ribs can be differentiated as distal cam rib 195 and proximal cam rib 197.

In one embodiment, as described herein, one end 198 of the proximal cam rib 197 acts as a mechanism for restricting movement (rotation) of the pinion gear 160 in one direction. More specifically, the housing 110 (inner frame, handle) can include an interference (a wall) 116 that stops and limits the rotation of the pinion gear 160 when its one end 198 of the proximal cam rib 197 makes contact (seats against) such wall 116 or other part. The pinion gear 160 is configured to rotate about 180 degrees and thus, the cam end 198 and the interference are formed such that the pinion gear 160 is prevented from being rotated more than about 180 degrees. In particular, a stop (interference) can be incorporated into any one of the components that make up the windup mechanism to limit its travel to about 180 degrees (the actuator assembly 125 stroke distance limits the instroke rotation angle of the windup assembly and the protrusion 116 limits the rotation angle of the windup assembly during the outstroke).

It will be understood that the pinion gear 160 exists as one part but can also be formed by adjoining multiple components to create the functions of a spring mount, gear, cams and internal ratchets.

In one embodiment, pinion gear 160 rotates about 180 degrees as the rack 180 is moved by operation of the actuator assembly 125. As just mentioned, the proximal cam end 198 on the pinion gear 160 engages the housing 110 in order to limit the rotation of the pinion gear 160 to about 180 degrees of movement. This stop (e.g., cam end 198) serves to stop the windup mechanism 140 after the energy in the windup mechanism is released. As described herein, a pawl 220 additionally controls the rotation and timing of the rotation of the pinion gear 160. The stop/interference point 116 can be thought of as being a zero point of the pinion rotation and the pawl engagement (described herein) as the 180 degree point.

In addition, the pinion gear 160 also rotationally engages a crankshaft ratchet 230. The crankshaft ratchet 230 is fixedly attached to an elongate crankshaft 240. In one embodiment, crankshaft ratchet 230 cannot rotate about crankshaft 240 due to mating features such as splines, keys, flats, set screw, etc. . . . and it cannot travel (slide) axially as it is constrained by the pinion gear 160 and the housing 110 or handle parts 112, 114. Similar to the pinion gear 160, the crankshaft ratchet 230 is a hollow structure that includes a first end (proximal) 232 and an opposite second end (distal) 234. As shown in the figures, the crankshaft ratchet 230 is disposed along the length of the crankshaft 240 such that a first portion of the crankshaft 240 extends outwardly from the second end 234 of the crankshaft ratchet 230. A second portion of the crankshaft 240 may extend outwardly from the first end 232 of the crankshaft ratchet 230 or it may terminate within the crankshaft ratchet 230.

Figure 3A:
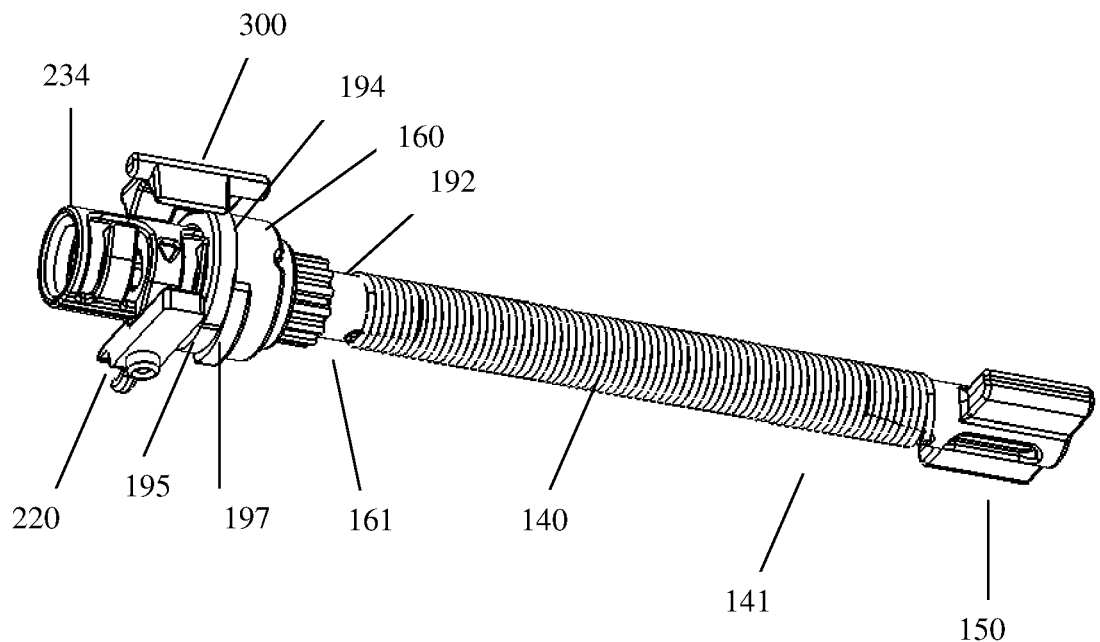
FIG. 3A is a side perspective view of a windup mechanism.
Figure 3B:
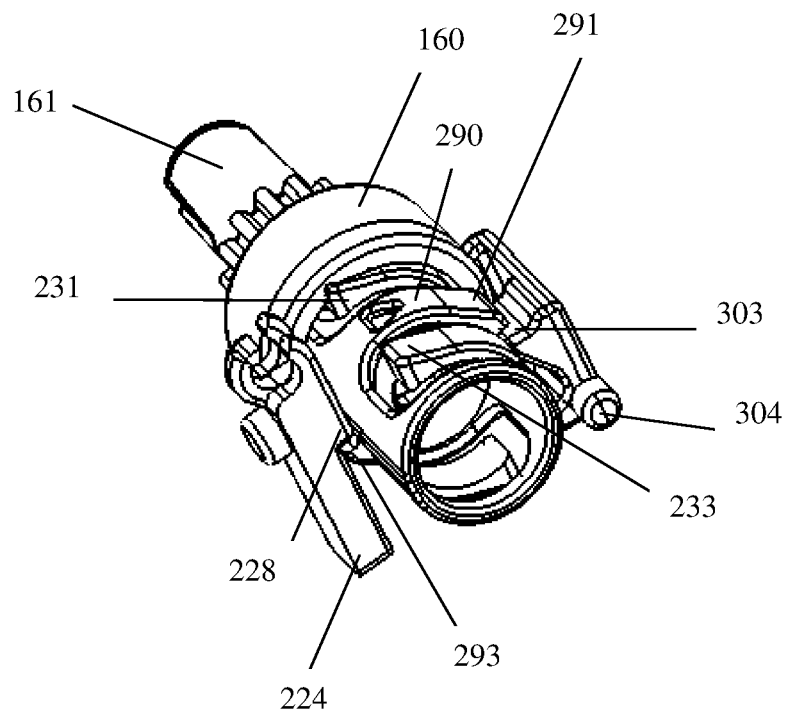
FIG. 3B is a perspective view of a pinion gear and crankshaft ratchet that form a part of the windup mechanism.
Figure 3C:
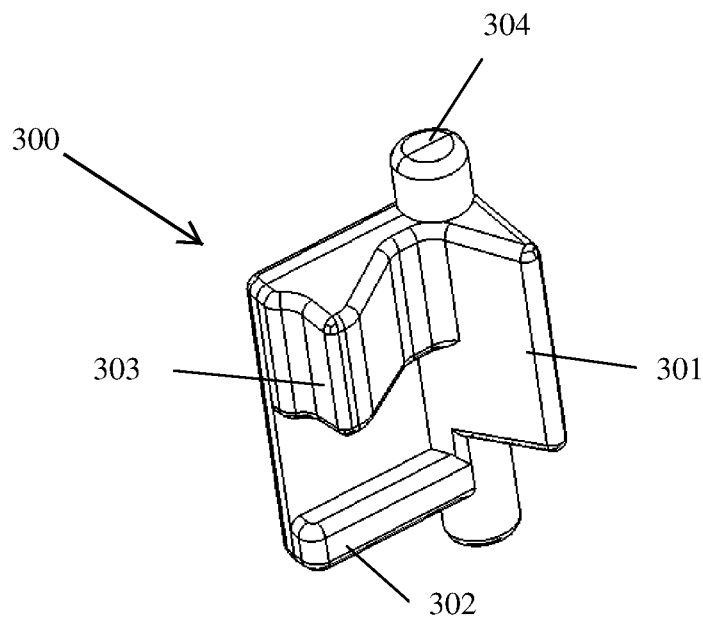
FIG. 3C is a side perspective view of a pivot stop.
Figure 3D:
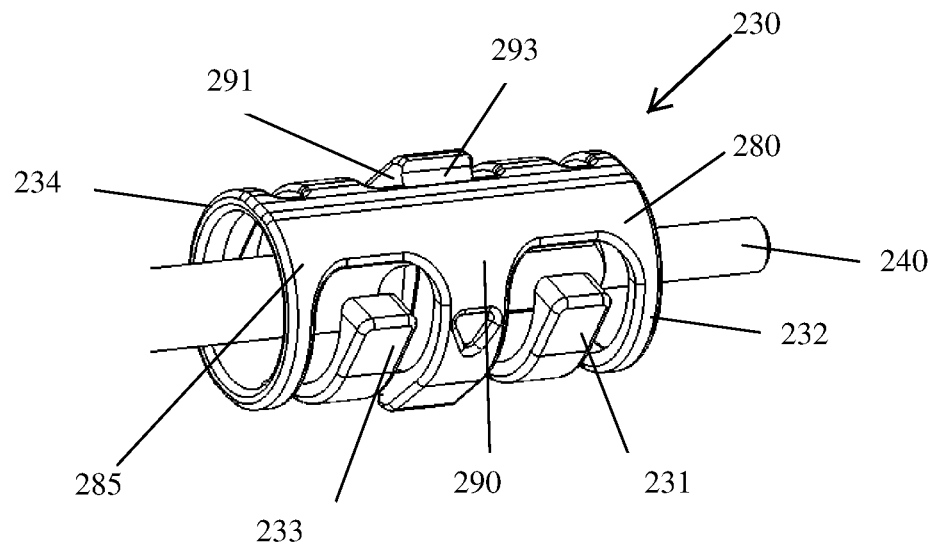
FIG. 3D is a side perspective view of the crankshaft ratchet disposed about the crankshaft.
Figure 3E:
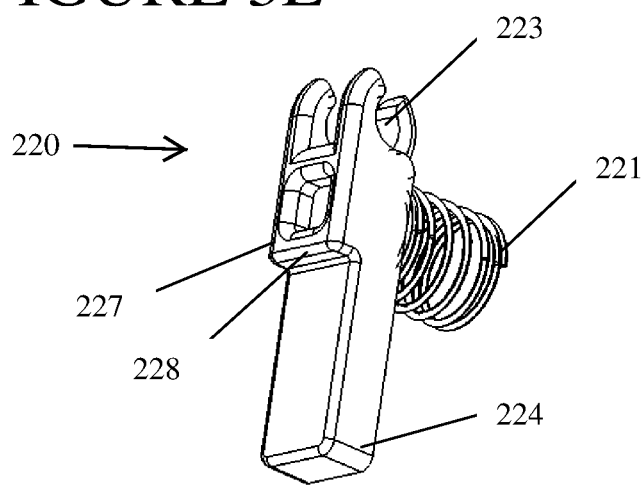
FIG. 3E is a perspective view of a pawl.

As shown in FIG. 3D, the crankshaft ratchet 230 includes a first end portion 280, a second end portion 285 and a center portion 290 that is located between the first and second end portions 280, 285. Each of the first end portion 280, second end portion 285, and center portion 290 thus extends circumferentially about the crankshaft 240. The first end portion 280 faces the pinion gear 160, while the second end portion 285 faces the gripping mechanisms 200, 210. The first end portion 280 has a pair of first flexible tabs 231 that can be in the form of flexible fingers that each has a beveled free end (cantilever). The flexible tabs 231 can be oriented about 180 degrees apart. The second end portion 285 can be a mirror image of the first end portion 280 and includes a pair of second flexible tabs 233 that can be in the form of flexible fingers that each has a beveled free end (cantilever).

Figure 4A:
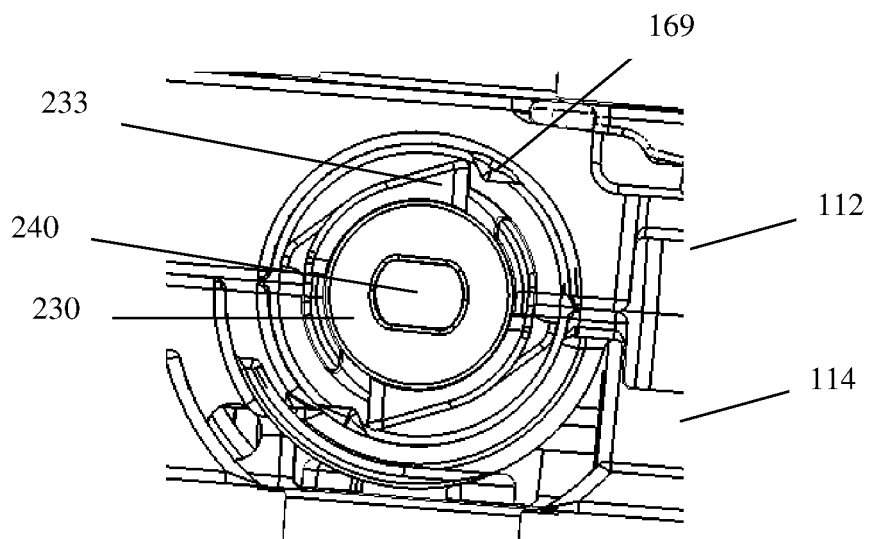
FIG. 4A is a cross-sectional view showing the crankshaft ratchet relative to the housing.
Figure 4B:
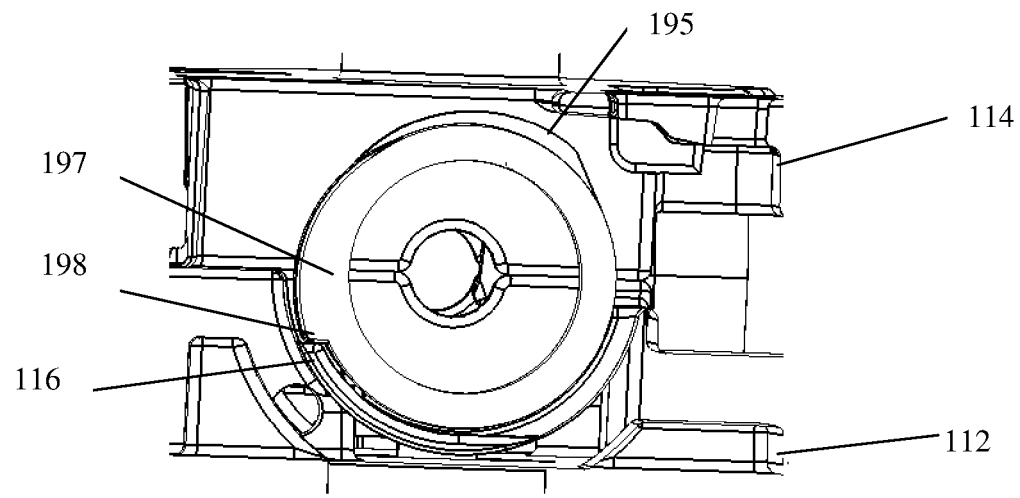
FIG. 4B is a cross-sectional view of the pinion gear relative to the housing.
Figure 4C:
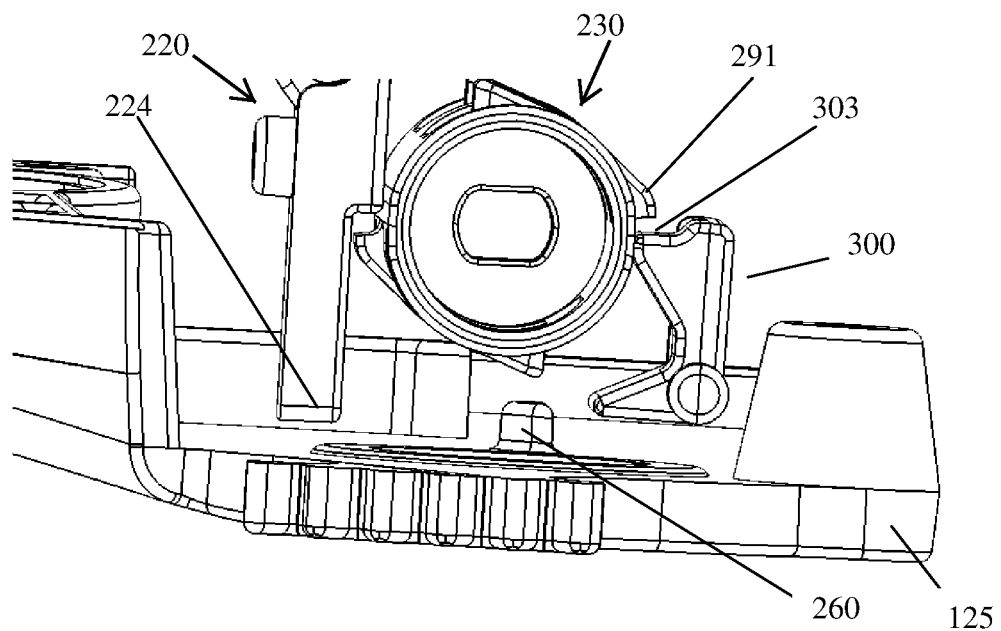
FIG. 4C is a cross-sectional view of the crankshaft ratchet relative to the pawl and pivot stop.
Figure 4D:
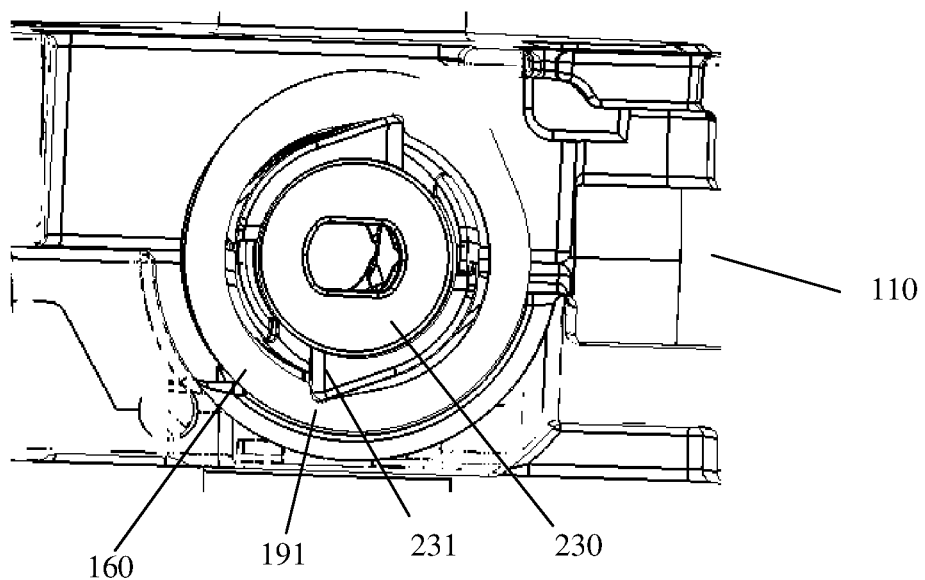
FIG. 4D is a cross-sectional view of the pinion and crankshaft ratchet.

As shown in FIG. 4C, the center portion 290 includes a pair of inflexible locking tabs 291 that are oriented about 180 degrees apart from one another. The locking tabs 291 have a beveled appearance that terminates in a locking surface 293. The locking tabs 291 face in opposite directions in that one locking surface 293 faces in one direction, while the other locking surface 293 faces in an opposite direction as shown. Locking tab 291 and its respective locking surface 293 will alternately contact pawl 220 and pivot stop 300 about every 180 degrees of rotation of the crankshaft ratchet 230. Therefore, one locking tab 291 and its surface 293 will be in contact or proximate to the pawl while the other locking tab 291 and its surface 293 will be in contact or proximate the pivot stop 300 at the end of each 180 degree rotation of the crankshaft 240. The pawl 220 is held in an open position by the actuator at the end of the outstroke of the actuator.

The first flexible tabs 231 are configured to selectively engage the notches (windows) 191 formed in the pinion gear 160 to selectively interlock the crankshaft ratchet 230 to the pinion gear 160 during operation of the actuator cycle(s). As described herein, when the crankshaft ratchet 230 is coupled to (interlocked with) the pinion gear 160, the rotation of the pinion gear 160 is translated to the crankshaft ratchet 230 and since the crankshaft 240 is attached to the crankshaft ratchet 230, the crankshaft 240 itself rotates in unison with the other coupled parts. As described herein, the movement (rotation) of the crankshaft 240 controls the operation of one aspect of the first and second gripping mechanisms 200, 210 to allow for the shuttle action of the needle 101 between the two gripping mechanisms 200, 210.

In the initial position of the device, the flexible tabs 231 are disposed within notches 191 of the pinion gear 160. During a first inward stroke of the actuator assembly 125, the pinion gear 160 is rotated in a first direction by the motion of the actuator 125 as described herein and this results in notches 191 of the windup ratchet 190 moving relative to the first flexible tabs 231 of the crankshaft ratchet 230, which remains fixed and stationary during the inward stroke due to a pivot stop 300, and or other elements such as tab 233. As the pinion gear 160 rotates, the tabs 231 flex and are disengaged from the respective notches 191 due to the cam surfaces (structures) of the tabs 231. At the end of the first inward stroke, the tabs 231 are placed in registration with notches 191 of the pinion gear 160 and the compressed tabs 231 spring into the notches, thereby releasably interlocking the two ratcheting elements 160, 230 to one another.

Figure 8:
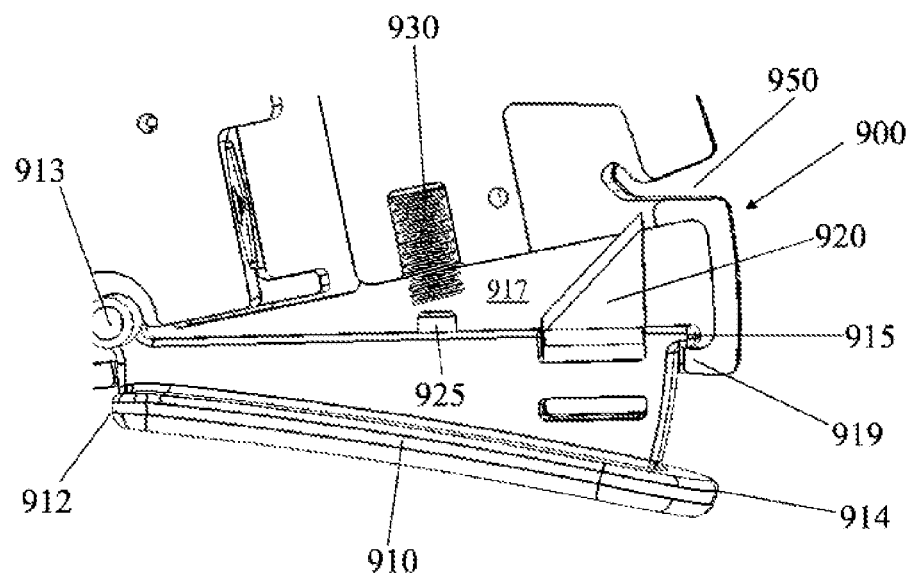
FIG. 8 is a cross-sectional view of an exemplary suture cutter.

As described below, the pawl 220 is unlatched during the initial rest position of the device and becomes latched during an inward stroke and this prevents the entire now linked assembly from moving (rotating). In addition, as shown in FIG. 4A, during the inward stroke of the actuator 125, the tabs 233 serve as an anti-reverse feature that prevents rotation of the crankshaft ratchet 230 during the inward stroke of the actuator 125. This results when the tabs 233 contact a stop 169 that is part of the housing (handle, inner frame) 110 as shown in FIG. 8.

When the actuator assembly 125 is released and it undergoes its out stroke action, the actuator 125 is returned to its initial rest position by means of the return spring 130. During almost the entire outstroke action, the releasably coupled pinion gear 160 and crankshaft ratchet 230 do not move, due to the stops (i.e., tabs 233) and other features described herein, until the pawl 220 is tripped as described herein at which time the windup mechanism 140 becomes released from the pawl 220 and spins (rotates) about 180 degrees in the opposite second direction due to the release of the stored energy of the torsion spring 141. It will be understood and is described herein that during the out stroke, the movable second gripping mechanism 210 moves.

When the user performs the next second inward stroke action of the actuator 125, the process repeats and the tabs 231 are released from the notches 191 due to the rotation of the windup ratchet 190 and the structure (cam edge) of the tabs 231. The windup mechanism stores energy and the pinion gear 160 rotates about 180 degrees before tabs 231 reengages notches (windows) 191, thereby fixedly (yet releasably) coupling the pinion gear 160 to the crankshaft ratchet 230 as described above.

As best shown in FIGS. 3A-4D, the pawl 220 is disposed within the housing 110 and has a degree of movement within the housing 110. More particularly, the pawl 220 pivots about a pivot 223 as shown in FIG. 3E. The pivot 223 is located at a first end of the pawl 220. The pawl 220 is biased by a biasing member 221, such as a spring, that applies a biasing force to the pawl 220. The spring 221 can be oriented horizontal or vertical and biases the pawl 220 into the crankshaft ratchet 230 for maintaining the crankshaft ratchet 230 and crankshaft 240 in a held position (no rotation), as seen in FIG. 4C.

The pawl 220 also includes a trip lever 224 that is in the form of a protrusion that extends outwardly from the pawl 220 at a second end opposite the first end. The trip lever 224 can have a rounded shape as shown. The pawl 220 also includes a step or locking member 227 that has a locking surface (a shoulder) 228 that is configured to selectively engage one of the locking tabs 291 formed in the center portion 290 of the crankshaft ratchet 230. More particularly, the step 227 serves to hold the windup mechanism in a cocked position. This windup mechanism and the crankshaft components can be thought of as being a linkage that operatively couples the actuator assembly 125 to the first and second gripping mechanisms 200, 210 for controllably moving each of the gripping mechanism between open and closed positions. As described herein, this cocked position is maintained until the trip lever 224 of the pawl 220 is actuated (tripped) by coming into contact with a trigger, which in the case of the illustrated embodiment is a protrusion (wall) that is part of the actuator assembly 125 of the suturing device 100. In particular, the actuator 125 includes a protrusion 260 formed therein that acts as a trip for the pawl 220. Alternatively, protrusion 260 could also be, among other things, a recess with a ledge that serves as the trip point. As understood, the actuator 125 is pivoting and thus the protrusion 260 is continuously moving during an inward stroke and an out stroke of the actuator 125. At the same time, the pawl 220 is pivotally mounted to the housing and the trip lever 224 is in plane with the protrusion 260. Thus, during the out stroke of the actuator 125, when the trip lever 224 contacts the protrusion 260, the pawl 220 pivots about pivot 223, thereby causing the locking member 227 to disengage from the locking tab 291 of the crankshaft ratchet 230. In particular, up until the final stage of the out stroke (e.g., during approximately the last 5% of movement of the actuator 125), the pawl 220 is engaged to the crankshaft ratchet 230; however, during this final stage, the pawl 220 is tripped as described herein and the pawl 220 disengages from the crankshaft ratchet 230, thereby allowing the crankshaft ratchet 230 to rotate as the stored energy is released.

Since the pawl 220 is functioning to hold the crankshaft ratchet 230 in its wound up (ready to fire) position, once the pawl 220 is released from the crankshaft ratchet 230, the crankshaft ratchet 230 releases its stored energy by rotating over a defined degree of travel (e.g., about 180 degrees). As will be understood, the crankshaft ratchet 230 rotates due to the release of energy stored by the torsion spring 141 since the crankshaft ratchet 230 is coupled thereto by its engagement with the pinion gear 160 (due to flexible tabs 231 being disposed in the notches 191). When the windup mechanism 140 is fired and releases its energy, the anti-reverse tabs 233 flex to allow rotation of the crankshaft ratchet 230 as will be appreciated in view of FIG. 4A. More specifically, the crankshaft ratchet 230 rotates in the second direction (e.g., counterclockwise in FIG. 4A) when the pawl 220 is tripped and the mechanism is fired and the cam structure and flexing properties of the tab 233 allows for such rotation in this second direction for the controlled about 180 degrees. Conversely, during the inward stroke, movement of the crankshaft ratchet 230 in the first direction (e.g., clockwise direction in FIG. 4A) is restricted by the anti-reverse tab 233 contacting the stop 169 of the housing 110. After the firing of the windup mechanism, tab 233 is freed of stop 169 and then resumes an engaged state with the stop 169 after about 180 degrees of rotation.

Pivot stop 300 is comprised of a distal cam follower 301, proximal cam follower 302, a locking step (stop) 303, and a pivot 304. In its simplest form, the pivot 304 is disposed within the housing (frame) 110 and can move (rotate) therein. The distal cam follower 301 is acted upon by the distal cam rib 195 of the pinion gear 160 to move (rotate) pivot stop 300 against locking tab 291 of crankshaft ratchet 230 and the proximal cam follower 302 is acted upon by the proximal cam rib 197 of the pinion gear 160 to move (rotate) pivot stop 300 away from locking tab 291 of crankshaft ratchet 230. Specifically, step 303 locks and unlocks the locking tab 291 of the crankshaft ratchet 230. The pivot stop 300 in addition to the pawl 220 and various notches, cams, stops, and flexible tabs of the pinion gear 160, housing 110 and the crankshaft ratchet 230 comprise a mechanism that positions (controls) the windup mechanism 140 and the crankshaft 240.

In one rotational direction, specifically created by the inward movement of the actuator assembly 125, pinion gear 160 slips past the crankshaft ratchet 230, whereas in the opposite rotational direction, the pinion gear 160 engages and rotates the crankshaft ratchet 230 during its rotation (near the end of the actuator return stroke in the illustrated embodiment). This one way clutch, comprised in this embodiment of the pinion gear 160, crankshaft ratchet 230, pivot stop 300 and pawl 220, is configured with synchronous, compliant and non-compliant protrusions and grooves, which control the rotation and timing of these components and the energy storage/release mechanism as described herein. For those skilled in the art, it is easy to conceive several one way clutch designs comprised of more or less similar components and features as described above for a needle transfer device and for other applications and uses. It is further understood that many forms of one-way clutches (rotors, pads, drums, diaphragm springs, pressure plates, hydraulic, centrifugal, electromagnetic, etc.) can be used to store and release energy in this or a similar design.

A rotatable, concentric bearing 250 (FIG. 5B) is affixed to a distal, eccentric portion of the crankshaft 240 and engages the first and second gripping mechanisms 200, 210 in order to create two synchronous clamping states (needle grip and needle release) as the crankshaft 240 rotates in about 180 degree increments. By mounting the bearing 250 in an eccentric manner, the bearing 250, as it moves (rotates), can contact one of the first and second gripping mechanisms 200, 210 and then as the bearing 250 continues to rotate, it contacts the other of the first and second gripping mechanisms 200, 210 (in an alternative embodiment, the bearing 250 could be designed to contact both mechanism 200, 210 at once in a disproportionate manner in that during the 0 and 180 degree states of the device, the load can be distributed disproportionately (e.g. 99/1) between the two mechanism 200, 210. As will be described below, the contact and motion of the bearing 250 against a portion of each of the first and second gripping mechanisms 200, 210 causes the respective gripping mechanism to move between a first clamping state (needle grip state) and a second clamping state (needle release state).

Eccentricity of the crankshaft 240 can be achieved with a concentric bearing and eccentric shaft or a concentric shaft and eccentric bearing, a single component featuring a shaft and bearing surface, a rotatable or fixed bearing, a bearing that is round or flat-edged, or any other obvious cammed shaft components and designs. In an alternative embodiment, there could be multiple bearings acting upon the respective gripping mechanisms 200, 210 instead of one central bearing (i.e., the concentric bearing 250). Also, staged bearings that work in tandem to first move the bearing 250 and gripping mechanisms 200, 210 nearly into its final position and then to use additional bearings to move the gripping mechanisms 200, 210 into its final position can be employed.

The device 100 features a mechanism to limit (restrict) the rotation of the crankshaft 240 to about 180 degrees (to keep the crankshaft in phase) during one actuator cycle of the actuator assembly 125 (similar to the other mechanisms described herein to limit rotation of the active parts to about 180 degrees during one actuator stroke). In a preferred embodiment, the stop 303 feature of the pivot stop 300 is moved (rotated) towards and away from locking tab 291 by means of the distal and proximal cam ribs 195, 197 of the pinion gear 160 contacting the distal and proximal cam followers 301, 302 of the pivot stop 300. When the crankshaft 240 rotates rapidly, e.g., as the stored windup energy is released as described herein, the stop 303 feature of the pivot stop 300 is rotated such that it interferes with (blocks) locking tab 291 of the crankshaft ratchet 230. Alternatively, a stop with a similar function could be positioned on the pinion gear 160 or other suitable component, in order to prevent over-rotation of the crankshaft 240.

As mentioned, the crankshaft ratchet 230 also engages pawl 220, which retains the crankshaft ratchet locking tab 291 in an energy stored state and then is later tripped by a protrusion 260 on the actuator assembly 125. It will be appreciated that other features in the actuator, gripping mechanism, housing, or other appropriate element may be used to trip the pawl. This tripping action of the pawl 220 (during the final stage of the outstroke of the actuator) releases the stored energy in the torsion spring 141, which instantaneously rotates the pinion gear 160, crankshaft ratchet 230, crankshaft 240, and bearing 250 about 180 degrees as a result of the coupling between these parts, as described herein, and this rotation of the bearing 250 activates one of the first and second gripping mechanisms 200, 210, while deactivating the other of the first and second gripping mechanisms 200, 210. This action effectively holds the needle 101 rigidly in one of the first and second gripping mechanisms 200, 210, while the other of the first and second gripping mechanisms 200, 210 releases the needle 101, thus, enabling the transfer of the needle between the first and second gripping mechanisms 200, 210.

As mentioned, there are two similar gripping mechanisms (first and second needle grippers) 200, 210 in the illustrated embodiment that grip the needle 101 in essentially the same manner. Each of the gripping mechanisms 200, 210 can be comprised of a stationary (fixed) gripper (jaw) 400 and a movable gripper (jaw) 410. It may also include a clamp fulcrum 411 or other mechanism, e.g., hinge pin, set screw, ledge, bar, pivot that enable leverage to be created and gripping to occur. Thus, a single point pivot can be provided and defined by a ball bearing or a set screw tip. In the case of the fulcrum 411 being a set screw (e.g., set screw tip) or other height adjustable member, the device 100 can be tuned to optimize the gripping force that the grippers 200, 210 exert upon the needle 101 and to allow unobstructed, clear entry of the needle into the clamp. In the case of a set screw tip or ball bearing driven by a set screw, the set screw can be torqued and driven through a hole in the fixed jaw into contact with the movable jaw to allow the position of the movable jaw relative to the fixed jaw to be adjusted (i.e., the gap between the two jaws can be adjusted and varied based on the movement of the set screw and the degree of which the set screw drives the movable jaw so as to either widen or decrease the gap distance between the two jaws).

This embodiment is one of many examples as to how gripping and transfer performance of gripping mechanisms 200, 210 can be optimized. In the case of an automated arrangement, the jaws can be automatically tuned by a suitable mechanism that acts on at least one of the jaws to allow the spacing between the two jaws at least when the jaws are in the closed position to be automatically adjusted (varied).

In other words, the jaw adjustment mechanism can be thought of as allowing for adjustment and control over a gap that is formed between the fixed jaw 400 and the movable jaw 410. This gap is selected to allow for entry of the needle when the jaws are in the open positions and it is selected so that when the jaws are in the closed positions, the needle is securely and firmly grasped by the two jaws. By constructing the clamp to permit adjustment of the distance of this gap, one can effectively "dial in" the clamp to the needle being used. There can be observed variances between needles and therefore, this feature allows a person to create the optimal gap between the two jaws.

Figure 5A:
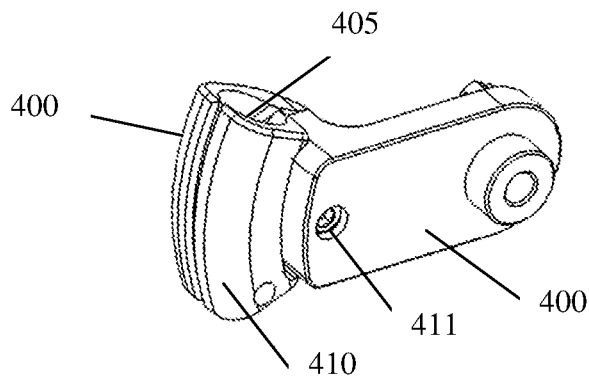
FIG. 5A is a perspective view of a needle gripper.
Figure 5B:
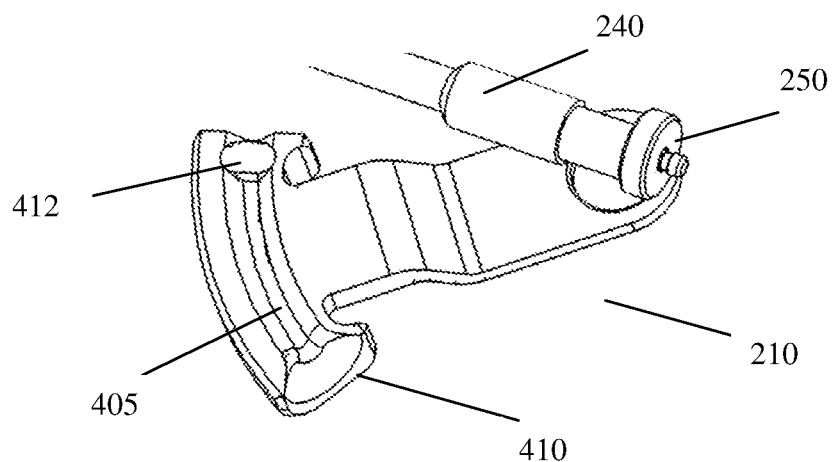
FIG. 5B is a perspective view of one part of the needle gripper along with the crankshaft.

As shown in FIGS. 5a-5b, the movable jaw 410 can function as a lever in that when a force is applied to one end of the movable gripper 410, the other end of the movable jaw 410 pivots on the point created by clamp fulcrum 411 allowing the needle gripper 200, 210 to close. The movable jaw (lever or pin) 410 is contacted by the bearing 250 and rotation of the bearing 250 selectively applies a force to the movable jaw 410 (such as pressing down on one end of the lever) resulting in movement of the movable jaw 410. In the illustrated embodiment, the bearing 250 contacts the movable jaw (lever) 410 and the rotation of the bearing 250 (as a result of the crankshaft 240 being driven) results in the jaw 410 being pushed down at one end causing the opposite end to pivot about pivot (fulcrum) 411.

In other words, in one aspect, the first and second grippers 200, 210 are adjustable to accommodate different sized (different diameters) needles. By being able to adjust one of the needle gripper parts (one jaw) relative to the other parts (other jaw), the characteristics (diameter) of the needle receiving channel can be altered and customized for the specific needle being used. Thus, for smaller diameter needles, the needle receiving channel's diameter can be reduced so that the smaller sized needle is securely held between the needle gripper parts in the closed position. If the characteristics (diameter) of the needle receiving channel were not adjustable, then it is possible that smaller needles could be loosely held. As mentioned, the adjustability of the jaws lets the user in effect "dial in" the proper spacing between the jaws for both the open and closed positions so that the needle can freely travel into the needle receiving channel when the jaws are opened and be actively gripped when the jaws are closed.

As shown, the static (fixed) jaw 400 can be a curved or multi-planar structure such that a distal section thereof is elevated relative to the proximal section. The static jaw 400 can have an opening formed therein through which the movable jaw 410 passes. The movable jaw 410 can be a straight, curved or multi-planar structure in that a proximal portion lies within a recess formed in the static jaw 400 and a distal portion passes through the window in the jaw 400. The distal end of the jaw 400 lies above the distal end of the jaw 410 and represents a top portion of the needle receiving clamp, either 200 or 210, while the distal end of the jaw 410 represents the bottom portion of the clamp. In an alternative embodiment, the static and moving jaws lay adjacent to one another without passing through one another.

As mentioned, the active (grip) condition and the default (release) condition are energized by the rotating crankshaft 240 and bearing 250 when this bearing 250 is at its high point and low point, respectively. In the current embodiment, the gripping force on the needle 101 can be altered by changing the diameter or degree of eccentricity of the bearing 250, which changes the displacement of the movable gripper 410. The gripping force can also be varied by modifying the distance relationship between the length of the lever arm of the movable gripper 410 and the length from the clamp fulcrum 411 to the gripping means needle groove 405. In this embodiment, the lever arm enables the device to amplify the load input into the gripping system at about a 3:1 ratio, although it is easy to recognize that higher or lower ratios can be utilized in order to provide a gripping force performance similar to a standard needle driver. Furthermore, the surface of the needle groove 405 can be altered with ribs, detents, notches, roughness, or similar modifications in order to enhance the gripping force on the needle 101 and to prevent the needle from pitching, rolling or pulling-out of the gripping means 200, 210.

It will be appreciated that the cross-sectional geometry (shape) of the groove 405 in the gripping means provides an effective gripping interface between the two at the location at which the two are in intimate contact. For example, the interface can be defined as a V-shaped notch, trapezoidal shape, flat, or other geometry thereby creating a matched or compatible fit between the needle and the gripping means. It will be appreciated that the shapes of the notch and needle can be different, i.e., round, oval, hexagonal, so long as there preferably is the above-described match fit between the two resulting in an effective needle gripping location. Further, the cross-sections of the needle and the receiving groove can be different from each other so as they achieve consistent alignment and sufficient gripping force.

Figure 6:
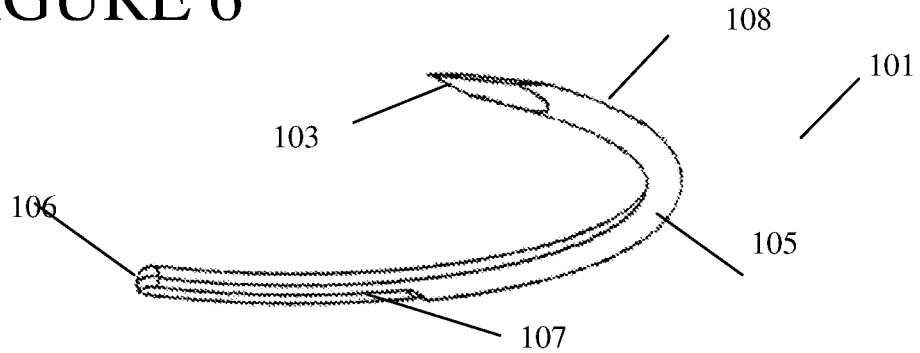
FIG. 6 is a perspective view of an exemplary pointed needle with a pair of flats.

In a specific embodiment presented in FIG. 6, the distal end 103 and proximal end 106 of the needle 101 may feature a pair of flats 107, 108 that are parallel and separated by the body 105 of the needle. These flats can be incorporated into many different needle cross-sections, e.g., round, triangle, annular, channeled, etc. . . . and serve to orient the needle 101 such that it is aligned with and between the pair of gripper mechanisms 200, 210 and can be transferred between the two mechanisms. The flats 107, 108 may be on opposite sides of the needle or on the same side. The flats may also prevent unwanted movement (twisting) of the needle 101 when held by the device 100.

The gripper can also feature a compliant or semi-compliant structure 412 that is integral to gripper 210 and serves to influence the travel (path) of the needle 101, as seen in FIG. 5B (e.g., due to contact with the needle during it movement in the needle receiving channel when it is received therein). Structure 412 can be fixedly mounted to the inside or outside of the gripper 210 and be aligned with (proximate to) groove 405 so long as the structure 412 influences and acts on the needle within the needle receiving channel. It can made from compliant materials (or semi-compliant materials) such as plastics, elastomers, rubber and other materials that will not damage the needle point 103 or allow the point to travel through its cross-section and injure a user. It will be appreciated that the housing and gripper parts are typically rigid since they are formed of plastics and/or metals, typically, and the needle is typically formed of a metal. Thus, the structure 412 is formed of a material that has a high compliancy compared to those rigid materials.

Typical materials for structure 412 include but are not limited to silicone, polyurethane elastomers, low-density polyethylene, polypropylene, acrylonitrile butadiene styrene, nylon, polyetheretherketone, polyisoprene and olefinic elastomers. Examples of methods to incorporate the structure 412 into the gripper 210 are insert molding, overmolding, casting, press-fitting, snap-fitting, dipping, swaging, extruding, etc. In one embodiment, the surface of the structure 412 is flat and normal to the needle point, however, there are many other configurations that will achieve the same function, e.g., round, oval, fenestrated, etc.

As shown, the compliant structure 412 can thus be in the form of a shaped material that is disposed relative to the needle receiving channel such that at least a portion, such as the pointed tip, of the needle contacts the compliant structure 412 during normal needle movements as the needle is shuttled from one gripper to the other gripper. In particular and according to one embodiment, the shaped material can be located such that when the needle is received within the needle receiving channel as during a transfer of the needle to one of the grippers, the shaped material influences the forward progression of the needle within the needle receiving channel or otherwise acts (e.g., guides, stops, compresses, restricts, etc.) on the needle as is travels within the respective gripper to ensure and optimize the needle movement within the channel. The shaped material can therefore, in one embodiment, be in the form of a plug or the like that is disposed within, along or proximate to the needle receiving channel and formed so as to influence the needle as it travels. As discussed herein, the manner in which the shaped material acts on the needle can be any number of different types of actions as mentioned above.

It will also be appreciated that while the figures show the compliant structure 412 incorporated into one of the needle grippers, both the fixed and movable needle grippers can include one compliant structure 412. In such arrangement, the compliant structures associated with the two grippers can be the same or they can have different shapes and/or be formed of different materials. The structure 412 can thus be formed in the fixed needle gripper at a location at which the proximal end of the needle can make contact therewith and the structure 412 associated with the movable gripper can be formed at a location at which the pointed distal end of the needle can make contact therewith.

It will also be understood that the location of the structure 412 is not limited to being the location shown in the FIG. 5B. While the structure 412 can be formed at the end of the needle receiving channel and be in the form of a block or plug or the like, the structure 412 can also be formed along the needle receiving channel between its ends. For example, the structure 412 can have an annular shape to permit an end portion of the needle to pass through but is configured to contact and engage another portion of the needle, thereby influencing the travel of the needle. For example, the annular shape can be sized so that the structure 412 contacts a tapered or wider portion of the needle to restrict or otherwise influence travel of the needle.

Figure 7A:
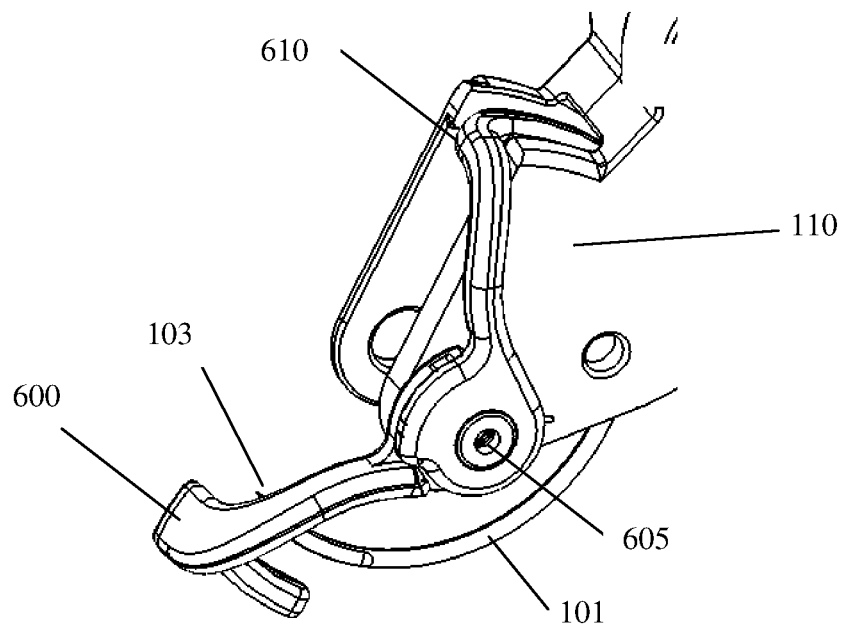
FIG. 7A is a perspective view of a pair of safety guards for shielding the needle.
Figure 7B:
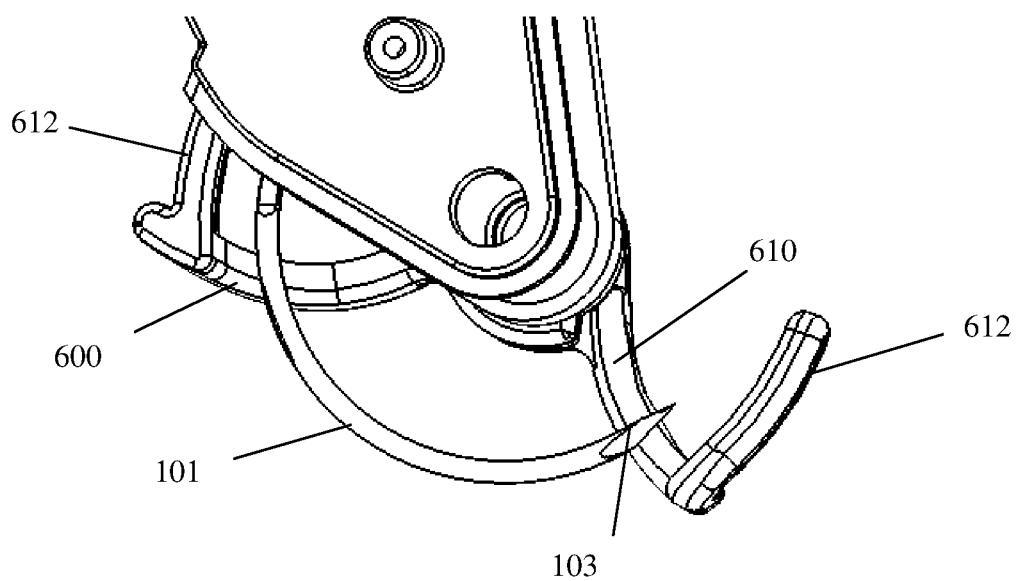
FIG. 7B is a perspective view of the safety guards.

There are two (first and second) safety guards 600, 610 depicted in FIGS. 7a-7b that are located at the distal end of the device 100 and protect the user from the sharp point 103 of the needle 100. In the illustrated embodiment the safety guards 600, 610 pivot on a shared axis 605, which is also the axis of rotation of the needle 101 and the axis about which the handle 110 pivots (rotates). The guards are biased to each other and to the housing 110 by torsion springs, although leaf springs, molded-in plastic springs, elastomers, and the like can create suitable biasing means. In the current device, the first safety guard 600 is biased to the housing (handle) 110 and shields the needle point 103 when the device 100 is in its at-rest position or when the second gripping means is retracted. Moreover, the second safety guard 610 is biased to the first safety guard 600 and shields the needle 101 from the user when the needle point 103 exits the tissue 10. The biased connections of the two safety guards 600, 610 enable the first safety guard 600 to rotate in concert with the device 100 as the user rotates the device into and through the tissue 10 and the second safety guard 610 to follow the first.

If during the operation of the device 100, the user reverses the rotational insertion of the needle 101 from the skin, the biasing means (springs) returns the safety guards 600, 610 to their original positions. The bias between the safety guards 600, 610 also allows them to flexibly and reversibly extend away from each other and contour themselves to the tissue being sutured. This can be particularly useful when the tissue is not flat. The second safety guard 610 is positioned away from the needle point 103 when the device 100 is at-rest, however, is seated on the tissue, and therefore protecting the user from the needle point when the needle 101 emerges from the tissue 10. In addition to protecting the user from the needle point, the second safety guard 610 also visually identifies the tissue exit location of the needle 101. In the current embodiment, the second safety guard 610 is comprised of a strut 612 that is physically aligned with the needle plane and provides visual location feedback to the user. It will be understood that other location identifiers alignment features such as cross-hairs, rings, slots, markings and the like can be utilized in order to achieve the same end. The strut of each safety guard 600, 610 thus provides an alignment feature to the user since the user understands that the needle 101 will travel closely and adjacently to the strut. For example, if the needle is being advanced through the tissue and is not visible, the user recognizes that the needle will exit the tissue 10 proximate to strut 612 of the safety guard 610 resting on the tissue.

The safety guards 600, 610 are merely exemplary and the guards can take any number of different forms so long as they perform the intended function. For example, the guards can be cage-like as disclosed in commonly owned U.S. patent application Ser. No. 13/584,536, which is hereby incorporated by reference in its entirety, or constructed from a frame-work of formed wire or plastic and can be formed of one or more components and its rotation may be constrained by a spring or other suitable means as shown. Further, the spring element may be integral to the framework, e.g., a wire form constructed of spring tempered steel or nickel titanium alloy which possess substantial elasticity. It features a spring bias that predisposes the shield towards covering the needle point when the device is in its ready to penetrate configuration. Alternatively, a tissue-contacting surface of each strut of the suture guards 600, 610 can include a modified surface (front and/or bottom surface of strut) that enhances gripping/interference between the guard and the tissue (or other object, like a catheter) so that the guard rotates away from the needle point and positions second guard at the needle exit site. The modified surface can be 3-D structures (barbs, dots, etc.) or can be rough surface or other texture that promotes enhanced gripping with tissue (skin).

Finally, a suture cutter that is integral to the handle would provide the user with a means to cut and trim suture 102 during the procedure. This suture cutter can take many forms including a static blade that slices the suture 102 as the suture is drawn across the blade, a linearly slideable blade, a pivoting blade, among others. FIG. 8 illustrates one embodiment that is a pivotable, non-linear actuated type. The cutter mechanism 900 includes a cutter body 910 that has a first end 912 that is pivotally attached to the housing 110 (at pivot 913) and an opposite second end 914 that is a free end. The cutter body 910 holds a blade 920 that faces inward toward the housing 110. The cutter body 910 includes a lip 915. The housing 110 includes a space 917 for receiving the cutter body 910 in the fully retracted cutting position thereof. The space 917 terminates at the proximal end of the housing 110 and includes a catch (lip) 919. The lip 915 is received within the space 917 and when the lip 915 contacts the catch 919, the outward movement of the cutter body 910 is limited since the engagement of lip 915 to catch 919 serves as a stop. A biasing member, such as a spring 930, is disposed within the housing 110 and is disposed partially within the space 917. The spring 930 is shown in a fully extended (rest) position in the figure. An inner surface of the cutter body 910 includes a protrusion 925 facing the housing 110. The protrusion constrains and supports the end of spring 930 when the cutter body 910 is pushed into the space 917 for cutting the suture 102. The blade 920 is received within a blade receiving space 917 of the housing 110 and a notch 950 is in communication with the blade receiving space 917. After the suture is cut by virtue of the user pressing the body 910, spring 930 returns the body 910 and blade 920 to its at-rest position, making it available to cut another suture 102.

In use of the preferred embodiment device 100, the user removes the device 100 from its sterile packaging in its at rest position with the needle tip enclosed by the second gripping mechanism 210 and the proximal end of the needle gripped by the first gripping mechanism 200. The user then grips the device 100. In a preferred embodiment, the user grips the device 100 between his/her thumb and one or more fingers with the user's thumb on the actuator assembly 125.

The user then depresses the actuator 125, retracting the second gripping mechanism 210, exposing the needle tip 103, and winding-up the energy storage mechanism 140.

The user then positions the needle tip 103 against the tissue 10 to be sutured and passes the needle tip 103 through the tissue 10 by rotating the housing 110 in an arcing motion until the needle tip 103 emerges from the tissue 10. The second safety guard 610 surrounds or shields the needle point 103 from the user as it exits the skin.

Next, the user slightly and controllably releases his grip on the actuator 125, allowing the return spring 130 to move the actuator 125 into its initial at-rest position, and, in so doing, rotates the second gripping mechanism 210 to re-engage the distal tip 103 of the needle 101. When the actuator 125 reaches the end of its out-stroke at the at-rest position, the pawl 220 releases the wound-up torsion spring energy in the energy storage mechanism, causing the crankshaft 240 and bearing 250 to rotate one half turn (i.e., 180 degrees), thereby switching the state of the gripping mechanisms 200, 210 such that the first gripping mechanism 200 is now released and the second gripping mechanism 210 grips the distal end 103 of the needle 101.

Next, the user depresses the actuator assembly 125. The second gripping mechanism 210, now gripping the needle 101, rotates from the at-rest position to the retracted position, and in so doing, actively and rotationally extracts the needle 101 from the tissue 10. This actuator movement also winds-up the energy storage mechanism for its next action.

Still depressing the actuator 125, the user lifts the device 100 from the tissue, pulling a length of suture 102 through the tissue 10. The user then releases his/her grip on the actuator 125, allowing it to rotate back to the at-rest position, and in so doing rotating the second gripping mechanism 210 to its at rest position, releasing the stored spring energy in the energy storage mechanism 140, rotating the crankshaft 240 and bearing 250, and switching the state of the gripping mechanisms 200, 210 to its original condition where the first gripping mechanism 200 grips the proximal end 103 of the needle 101 and the second gripping mechanism 210 has released the needle 101, yet still covers the needle point 103.

Finally the user ties the suture 102 to form a stitch and trims the suture near the knot, leaving the user holding the device 100 in exactly the same condition as when it was removed from the package, except for a slightly shorter length of suture. The device 100 is now ready to deliver additional sutures.

Based on the foregoing, it will be appreciated that the device 100 provides a single actuator that can be used with one hand and allows the user to complete one actuator cycle by pressing and then releasing the single actuator two times. All of this can be done with a single hand during the procedure. In addition, the present device can be provided such that the actuator and cutter can be located on the same side of the device to allow the user to use the same thumb to operate both.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for suturing tissue comprising:
   a handle including a housing having a distal end and an opposite proximal end;
   a suturing needle for advancing a suture through the tissue, the suturing needle having a first pointed end and an opposite second end;
   a first needle gripper coupled to the housing, the first needle gripper being configured to both grasp and release the suturing needle;
   a second needle gripper coupled to the housing, the second needle gripper being configured to both grasp and release the suturing needle; and
   an actuator that is pivotally coupled to the housing, the actuator being operatively coupled to the second needle gripper for moving the second needle gripper between a fully extended position and a retracted position relative to the housing;
   a one-way clutch that is operatively coupled to the actuator, the one-way clutch including an energy storage member and a pinion gear coupled to the energy storage member, the pinion gear selectively engaging a crankshaft ratchet that is coupled to a rotatable crankshaft that controllably rotates in defined increments to synchronously alter the states of the first needle gripper and the second needle gripper to permit each of the first needle gripper and the second needle gripper to either (a) receive and grasp the suturing needle or (b) release the suturing needle; and
   a stop mechanism that is configured to limit a degree of travel of the crankshaft so that the crankshaft rotates in the defined increments, the stop mechanism including a first stop that is engaged by the pinion gear and a second stop that is engaged by the crankshaft ratchet.

2. The device of claim 1, wherein the one-way clutch is configured to trip at a select operating state of the actuator to cause a release of stored energy in the energy storage member which causes the synchronized alteration of the states of the first needle gripper and second needle gripper.

3. The device of claim 2, wherein the actuator includes a protrusion that acts as a trip for the one-way clutch.

4. The device of claim 1, further including a rack that is coupled to but separate from the actuator such that the rack and actuator move together and the rack is continuously coupled to the pinion gear.

5. The device of claim 4, further including a return spring coupled to the actuator for generating an outstroke of the actuator as a result of generating a return force for returning the actuator to an initial position, wherein in an inward stroke of the actuator, the actuator contacts and drives the rack from an initial rest position, while during the outstroke of the actuator, the rack remains in a cocked position until stored energy of the one-way clutch is released at which time, the rack returns to the initial rest position.

6. The device of claim 1, wherein an interior of the pinion gear includes a first notch and a second notch spaced from the first notch and wherein an exterior of the pinion gear includes a proximal cam rib and a distal cam rib spaced from the proximal cam rib, the first notch and second notch being configured to selectively receive protrusions formed as par of the crankshaft ratchet for selectively coupling the pinion gear to the crankshaft ratchet, wherein the proximal cam rib selectively engages the first stop for limiting a degree of rotation of the pinion gear.

7. The device of claim 6, wherein the first notch and second notch are formed about 180 degrees apart from one another and each of the proximal cam rib and the distal cam rib extending circumferentially about the exterior of the pinion gear.

8. The device of claim 6, wherein the protrusions comprise a pair of spaced apart flexible first and second tabs formed about an exterior of the crankshaft ratchet, wherein reception of the flexible first and second tabs within the respective first and second notches causes the pinion gear and crankshaft ratchet to be coupled to one another and permit rotation of the coupled pinion gear and crankshaft ratchet as a single unit.

9. The device of claim 8, wherein the first and second tabs are formed about 180 degrees apart.

10. The device of claim 8, wherein the crankshaft ratchet further includes a third tab and a fourth tab that selectively engage the second stop.

11. The device of claim 10, wherein the second stop comprises a pivot stop, wherein the pivot stop includes a distal cam follower that is acted upon by the distal cam rib to pivot the pivot stop into engagement against one of the third and fourth tabs of the crankshaft ratchet and a proximal cam follower that is acted upon by the proximal cam rib to pivot the pivot stop away from the third or fourth tab, the pivot stop further including a stop member that selectively engages one of the third tab and the fourth tab of the crankshaft ratchet.

12. The device of claim 11, wherein each of the third tab and the fourth tab alternatively contacts a pivotable pawl and the pivot stop about every 180 degrees of rotation of the crankshaft ratchet, wherein the pivotable pawl selectively engages the crankshaft ratchet for both maintaining stored energy in the one-way clutch and for releasing the stored energy when the pawl is tripped.

13. The device of claim 1, wherein the first stop is formed as part of the housing.

14. The device of claim 1, wherein the stop mechanism is configured to limit a degree of travel of the crankshaft to 180 degrees.

15. The device of claim 1, wherein the second stop is configured to restrict movement of the crankshaft ratchet after the crankshaft ratchet is tripped and releases stored energy.

16. The device of claim 1, wherein the second stop comprises a movable part that moves between a first position in which the second stop is disengaged from the crankshaft ratchet and a second position in which the second stop is located within the path of the crankshaft ratchet and serves to restrict movement of the crankshaft ratchet.

17. The device of claim 16, wherein the movable part moves between the first position and the second position as a result of contact with the pinion gear to cause pivoting of the second stop.

18. The device of claim 17, wherein the second stop includes a distal cam follower that is contacted by the pinion gear to move the second stop to the first position and a proximal cam follower that is contacted by the pinion gear to move the second stop to the second position.

19. The device of claim 16, wherein the second stop rotates about an axis that is parallel to a longitudinal axis of the crankshaft.

20. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and an actuator that is coupled to the housing, wherein the actuator is configured such that operation of the actuator causes: (a) the second needle gripper to pivot between a fully extended position and a retracted position relative to the housing; and (b) a state of each of the first and second needle grippers to be altered to permit each respective needle gripper to either: (i) receive and grasp the suturing needle or (ii) release the suturing needle;
wherein each of the first and second needle grippers comprises a first clamp and a second movable clamp that is pivotally attached to the first clamp at a pivot to permit the second movable clamp to pivot between open and closed positions, each of the first clamp and the second movable clamp defining a needle receiving groove in which the suturing needle is captured, the needle receiving grooves of the first clamp and the second movable clamp defining a needle receiving channel, wherein the first clamp and the second movable clamp are adjustable relative to one another to permit a size of the needle receiving channel to be varied and set.

21. The device of claim 20, wherein an adjustment mechanism is provided between the first clamp and the second movable clamp for adjusting positions between the first clamp and the second movable clamp so as to vary a diameter of the needle receiving channel when the first clamp and second movable clamp are in the closed positions.

22. The device of claim 21, wherein the adjustment mechanism comprises a clamp fulcrum in the form of a set screw that adjusts a gap distance between the first clamp and the second movable clamp.

23. The device of claim 22, wherein the first clamp is a fixed clamp and the second clamp is a movable clamp and the set screw passes through the fixed clamp and into contact with the movable jaw, whereby a position of the movable jaw relative to the fixed jaw to be varied, thereby changing the gap distance.

24. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is pivotally coupled to the housing, the actuator being operatively coupled to the second needle gripper for moving the second needle gripper between a fully extended position and a retracted position relative to the housing;
an energy storage assembly that is configured to controllably move in defined increments to synchronously alter the states of the first needle gripper and the second needle gripper to permit each of the first needle gripper and the second needle gripper to either (a) receive and grasp the suturing needle or (b) release the suturing needle; and
a stop mechanism that is configured to limit a degree of travel of the energy storage assembly so that the energy storage assembly moves in the defined increments, the stop mechanism including a movable stop member that moves between a first position in which the movable stop member is disengaged from the energy storage assembly to allow the energy storage assembly to move and store energy and a second position in which the movable stop member assumes a position that is in the path of the energy storage assembly such that when the energy storage assembly is tripped and releases the stored energy, the energy storage assembly is driven into contact with the movable stop member, thereby restricting movement of the energy storage assembly.

25. The device of claim 24, wherein the energy storage assembly includes a one-way clutch that is operatively coupled to the actuator, the one-way clutch including an energy storage member and a pinion gear coupled to the energy storage member, the pinion gear selectively engaging a crankshaft ratchet that is coupled to a rotatable crankshaft that controllably rotates in defined increments to synchronously alter the states of the first needle gripper and the second needle gripper to permit each of the first needle gripper and the second needle gripper to either (a) receive and grasp the suturing needle or (b) release the suturing needle.

26. The device of claim 25, wherein in the first position, the movable stop member is disengaged from the crankshaft ratchet and in the second position the movable stop member is located within the path of the crankshaft ratchet.

27. The device of claim 25, wherein the movable part moves between the first position and the second position as a result of contact with the pinion gear to cause pivoting of the movable stop member.

28. The device of claim 25, wherein the movable stop member includes a proximal cam follower that is contacted by the pinion gear to move the movable stop member to the first position and a distal cam follower that is contacted by the pinion gear to move the movable stop member to the second position.

29. A device for suturing tissue comprising:
a suturing needle for advancing a suture through the tissue, the suturing needle having a first pointed end and an opposite second end;
a first needle gripper coupled to a housing the first needle gripper being configured to both grasp and release the suturing needle;
a second needle gripper coupled to the housing, the second needle gripper being configured to both grasp and release the suturing needle; and
an actuator that is coupled to the housing, wherein the actuator is configured such that operation of the actuator causes: (a) the second needle gripper to pivot between a fully extended position and a retracted position relative to the housing; and (b) a state of each of the first and second needle grippers to be altered to permit each respective needle gripper to either: (i) receive and grasp the suturing needle or (ii) release the suturing needle; and
wherein at least one of the first and second needle grippers includes a compliant structure fixedly attached to the at least one of the first and second needle grippers within a needle receiving channel that is formed in the at least one of the first and second needle grippers, the needle receiving channel having a first section that includes an entrance into the needle receiving channel and a second section spaced from the entrance, the entrance of the needle receiving channel being open along an exposed face of the at least one of the first and second needle grippers, the compliant structure being disposed at a fixed location within only the second section of the needle receiving channel for influencing travel of the needle within the needle receiving channel.

30. The device of claim 29, wherein the compliant structure is formed of a compliant material that is disposed relative to the needle receiving channel such that an end portion of the needle contacts the compliant material during an actuation cycle, thereby influencing the travel of the needle.

31. The device of claim 30, wherein the compliant material is selected from the group consisting of: silicone, polyurethane elastomers, low-density polyethylene, polypropylene, acrylonitrile butadiene styrene, nylon, polyetheretherketone, polyisoprene and olefinic elastomers.

32. The device of claim 29, wherein an end surface of the compliant structure that faces the needle is flat and normal to the first pointed end of the needle.

33. The device of claim 32, wherein the end surface is positioned so that it can be contacted by the first pointed end of the needle during travel within the needle receiving channel.

34. The device of claim 29, wherein the needle receiving channel is defined by a pair of side walls, the compliant structure extending from one side wall to the other side wall resulting in a surface of the compliant structure that is contactable by the needle being located normal to one of the first pointed end and the opposite second end of the needle.

35. The device of claim 34, wherein the surface of the compliant structure is located normal to the first pointed end.

36. The device of claim 29, wherein the compliant structure defines an end of the needle receiving channel that is opposite the entrance of the needle receiving channel.

37. The device of claim 29, wherein each of the first and second needle grippers includes one compliant structure, the compliant structure of the first needle gripper being positioned for influencing the second end of the needle, while the compliant structure of the second needle gripper being positioned for influencing the first pointed end of the needle.

38. The device of claim 29, wherein the second section of the needle receiving channel is formed of a first material and the compliant structure is formed of a different second material, the compliant structure overlying the needle receiving channel.

39. A device for suturing tissue comprising:
a suturing needle for advancing a suture through the tissue, the suturing needle having a first pointed end and an opposite second end;
a first needle gripper coupled to a housing, the first needle gripper being configured to both grasp and release the suturing needle;
a second needle gripper coupled to the housing, the second needle gripper being configured to both grasp and release the suturing needle; and
an actuator that is coupled to the housing, wherein the actuator is configured such that operation of the actuator causes: (a) the second needle gripper to pivot between a fully extended position and a retracted position relative to the housing; and (b) a state of each of the first and second needle grippers to be altered to permit each respective needle gripper to either: (i) receive and grasp the suturing needle or (ii) release the suturing needle; and
wherein at least one of the first and second needle grippers includes a needle influencing element that comprises a shaped structure on at least one of the first and second needle grippers within a needle receiving channel that is formed in the at least one of the first and second needle grippers, the needle receiving channel having a first section that includes an entrance into the needle receiving channel and a second section spaced from the entrance, the entrance of the needle receiving channel being open along an exposed face of the at least one of the first and second needle grippers, the needle influencing element being disposed at a fixed location that is located within the second section of the needle receiving channel spaced from the entrance into the needle receiving channel, the first section of the needle receiving channel being free of the needle influencing element, the needle influencing element being configured to influence travel of the needle within the needle receiving channel after the needle has passed through the entrance of the needle receiving channel.

40. The device of claim 39, wherein the needle influencing element is spaced inward from an end of the needle receiving channel that is opposite the entrance into the needle receiving channel.

41. The device of claim 39, wherein the needle influencing element is formed of a material that is different than a material of the at least one of the first and second needle grippers in which the needle receiving channel is formed.

* * * * *